US011352879B2

(12) United States Patent
Li et al.

(10) Patent No.: US 11,352,879 B2
(45) Date of Patent: Jun. 7, 2022

(54) COLLABORATIVE SENSING AND PREDICTION OF SOURCE ROCK PROPERTIES

(71) Applicant: Saudi Arabian Oil Company, Dhahran (SA)

(72) Inventors: Weichang Li, Katy, TX (US); Sebastian Csutak, Houston, TX (US); David Jacobi, Houston, TX (US); Tiffany Dawn McAlpin, Richmond, TX (US); Max Deffenbaugh, Richmond, TX (US); Shannon Lee Eichmann, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 468 days.

(21) Appl. No.: 15/921,003

(22) Filed: Mar. 14, 2018

(65) Prior Publication Data
US 2018/0347354 A1 Dec. 6, 2018

Related U.S. Application Data

(60) Provisional application No. 62/471,274, filed on Mar. 14, 2017.

(51) Int. Cl.
*E21B 49/00* (2006.01)
*G06N 20/00* (2019.01)
(Continued)

(52) U.S. Cl.
CPC ....... *E21B 49/003* (2013.01); *G01N 21/3563* (2013.01); *G01N 33/241* (2013.01);
(Continued)

(58) Field of Classification Search
CPC .. G01N 21/3563; G01N 33/24; G01N 33/241; G01N 2021/3595; E21B 49/003
See application file for complete search history.

(56) References Cited

U.S. PATENT DOCUMENTS 4,593,197 A * 6/1986 Miyatake ........... G01N 21/3504
250/338.3
6,629,086 B1 * 9/2003 Lafargue .............. G01N 33/241
706/2
(Continued)

FOREIGN PATENT DOCUMENTS

| GB | 2344172 A | 5/2000 |
| WO | 2009142873 | 11/2009 |
| WO | 2011133421 A2 | 10/2011 |

OTHER PUBLICATIONS

Alizadeh B. et al.: "Artificial neural network modeling and cluster analysis for organic facies and burial history estimation using well log data: A case study of the South Pars Gas Field", Computers and Geosciences, vol. 45, 23, pp. 261-269.
(Continued)

*Primary Examiner* — Michael J Dalbo
(74) *Attorney, Agent, or Firm* — Bracewell LLP; Constance G. Rhebergen; Brian H. Tompkins

(57) ABSTRACT

Systems, apparatuses, and computer-implemented methods are provided for the sensing and prediction of properties of source rock. Disclosed here is a method of predicting the maturity of a source rock that includes obtaining a plurality of data of a sample source rock from a plurality of data acquisition devices placed in vicinity of the sample source rock and analyzing the received data using a predictive correlation to determine maturity of the sample source rock. The predictive correlation is generated by applying a machine learning model to correlate the plurality of data acquired from a plurality of representative source rocks with
(Continued)

a plurality of properties of the plurality of representative source rocks.

30 Claims, 32 Drawing Sheets

(51) Int. Cl.
*G16C 20/30* (2019.01)
*G06N 20/20* (2019.01)
*G01N 21/3563* (2014.01)
*G01N 33/24* (2006.01)
*G06N 5/04* (2006.01)
*G16C 20/70* (2019.01)
*G01N 21/35* (2014.01)

(52) U.S. Cl.
CPC .............. *G06N 5/046* (2013.01); *G06N 20/00* (2019.01); *G06N 20/20* (2019.01); *G16C 20/30* (2019.02); *G01N 33/24* (2013.01); *G01N 2021/3595* (2013.01); *G16C 20/70* (2019.02)

(56) References Cited

U.S. PATENT DOCUMENTS

| | | | |
|---|---|---|---|
| 6,932,155 B2 | 8/2005 | Vinegar et al. | |
| 7,853,045 B2 | 11/2010 | Nishioka | |
| 8,073,623 B2 | 12/2011 | Hartmann et al. | |
| 8,738,295 B2 | 5/2014 | Baez et al. | |
| 9,229,126 B2 | 1/2016 | Perkins | |
| 9,488,605 B2 | 11/2016 | Feser et al. | |
| 9,528,364 B2 | 12/2016 | Samuel et al. | |
| 2005/0043630 A1* | 2/2005 | Buchert | A61B 5/14532 600/473 |
| 2011/0139989 A1* | 6/2011 | Pawlak | G01J 5/34 250/340 |
| 2012/0095687 A1 | 4/2012 | Lecompte | |
| 2013/0262069 A1 | 3/2013 | Leonard | |
| 2014/0088876 A1 | 3/2014 | Shiley | |
| 2014/0365409 A1* | 12/2014 | Burch | E21B 43/00 706/12 |
| 2015/0153470 A1 | 6/2015 | Stove et al. | |
| 2016/0069177 A1* | 3/2016 | Badri | E21B 49/00 250/269.1 |
| 2016/0084817 A1 | 3/2016 | Lawson et al. | |
| 2016/0349174 A1* | 12/2016 | Washburn | G01N 33/28 |
| 2017/0329045 A1* | 11/2017 | Myers | G06T 7/0004 |
| 2018/0188161 A1* | 7/2018 | Craddock | G01N 33/28 |
| 2019/0227087 A1* | 7/2019 | Belani | G01N 33/241 |

OTHER PUBLICATIONS

International Search Report and Written Opinion for related PCT application PCT/US2018/022293 dated Jul. 10, 2018.
El-Sebakhy E. A. et al.:, "Forecasting PVT properties of crude oil systems based on support vector machines modeling scheme",Journal of Petroleum Science and Engineering, vol. 64, No. 1-4, Feb. 1, 2009, pp. 25-34.
Esmaili S. et al.: "Full field reservoir modeling of shale assets using advanced data-driven analytics", Geoscience Frontiers, Elsevier, Amsterdam, NL, vol. 7, No. 1, Jan. 23, 2015, pp. 11-20.
Shi X. et al: "Application of extreme learning machine and neural networks in total organic carbon content prediction in organic shale with wire line logs", Journal of Natural Gas Science and Engineering, vol. 33, May 24, 2016, pp. 687-702.
Fisher, et al., Chemical recognition with broadband THz spectroscopy; Proceedings of the IEEE; 2007; vol. 95, No. 8, pp. 1592-1604.
Ganz, et al., IR classification of kerogen type, thermal maturation, hydrocarbon potential and lithological characteristics; Journal of Southeast Asian Earth Sciences, 1991, vol. 5, Nos. 1-4, pp. 19-28.
IEEE Transactions on Geoscience and Remote Sensing, A Publication of the IEEE Geoscience and Remote Sensing Society; Aug. 2015; vol. 53, No. 8, pp. 4259-4274.
Radke, et al.. Maturity parameters based on aromatic hydrocarbons: Influence of the organic matter type; Organic Geochemistry; 1986, vol. 10, Nos. 1-3, pp. 51-63.
Seewald, U.S., Organic-inorganic interactions in petroleum-producing sedimentary basins; Nature, Nov. 2003, vol. 426, pp. 327-333.
Stephani, et al., Wavelet-Based Dimensionality Reduction for Hyperspectral THz Imaging; Terahertz Science and Technology, Sep. 2010, vol. 3, pp. 117-129.
Walther, M., Modern Spectroscopy on Biological Molecules: Structure and Bonding Investigated by THz Time-domain and Transient Phase-grating Spectroscopy; Inaugural Dissertation; Nov. 2003.
Washburn, et al., Detailed Description of Oil Shale Organic and Mineralogical Heterogeneity via Fourier Transform Infrared Microscopy; Energy & Fuels; 2015, vol. 29, No. 7, pp. 4264-4271.

* cited by examiner

Data & Predictions

| | AdaBoost | Random Forest Regression | HI_%Ro | sampleName |
|---|---|---|---|---|
| 1 | 0.000 | 0.000 | 0.000 | illite150T1 |
| 2 | 0.000 | 0.000 | 0.000 | illite150T2 |
| 3 | 0.000 | 0.000 | 0.000 | kaolinite106um |
| 4 | 0.000 | 0.000 | 0.000 | kaolinite150T1 |
| 5 | 0.000 | 0.000 | 0.000 | kaolinite150T2 |
| 6 | 0.000 | 0.000 | 0.000 | mont45um |
| 7 | 0.000 | 0.000 | 0.000 | mont63um |
| 8 | 0.000 | 0.000 | 0.000 | mont75um |
| 9 | 0.000 | 0.000 | 0.000 | montmorillonite150T1 |
| 10 | 0.000 | 0.000 | 0.000 | montmorillonite150T2 |
| 11 | 0.000 | 0.000 | 0.000 | montmorillonite150T3 |
| 12 | 1.590 | 1.658 | 1.590 | sample 1A |
| 13 | 1.590 | 1.658 | 1.590 | sample 2A |
| 14 | 1.590 | 1.658 | 1.590 | sample 2B |
| 15 | 1.020 | 1.137 | 1.020 | sample 2C |
| 16 | 0.630 | 0.910 | 0.630 | sample 3A |
| 17 | 2.160 | 1.791 | 2.160 | sample 4A |
| 18 | 2.160 | 1.791 | 2.160 | sample 4B |

FIG. 21

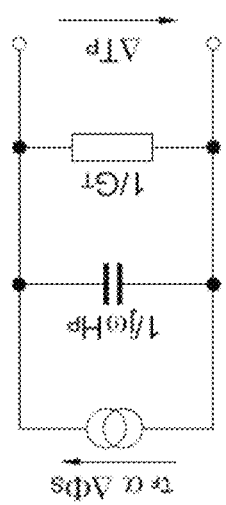
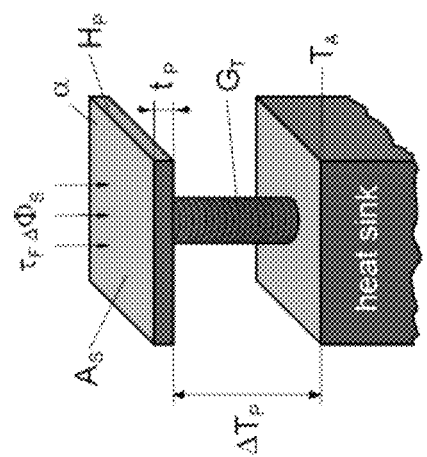
FIG. 22A
FIG. 22B

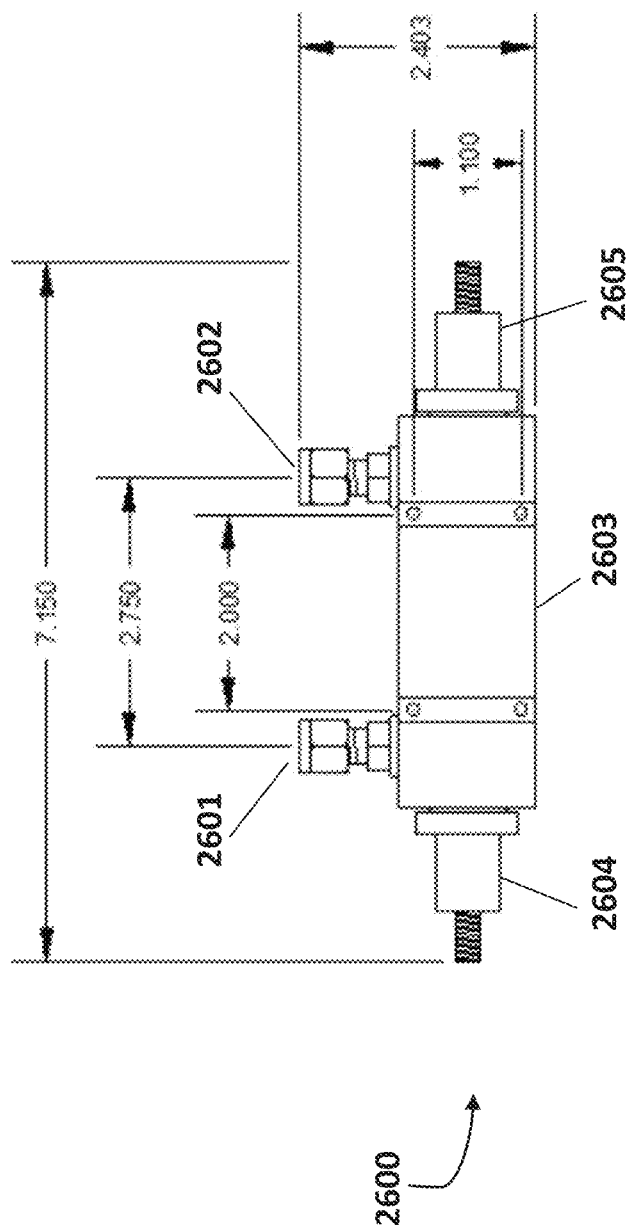

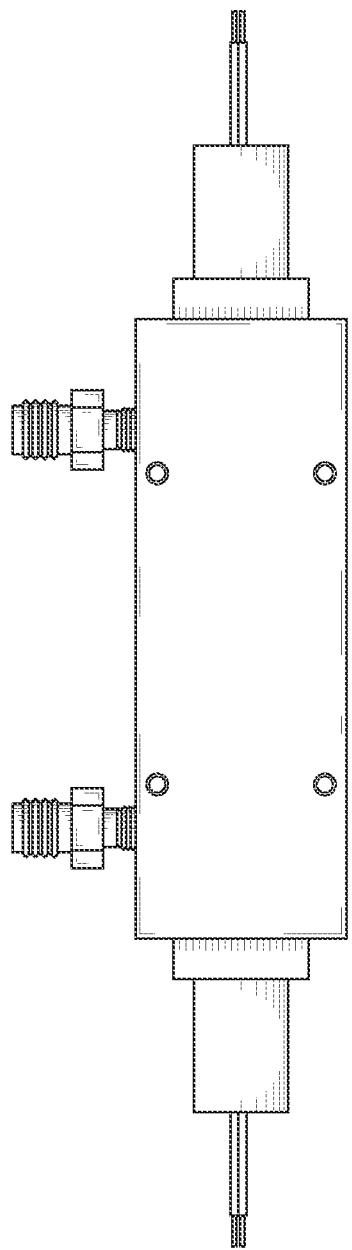
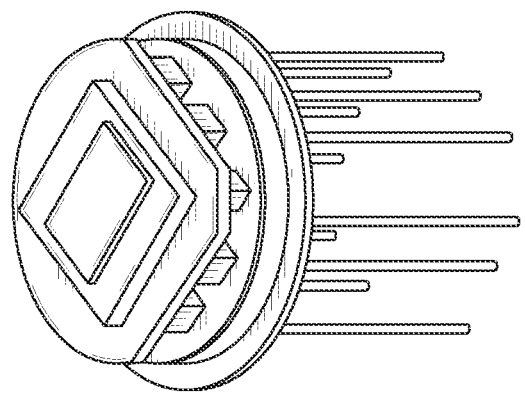
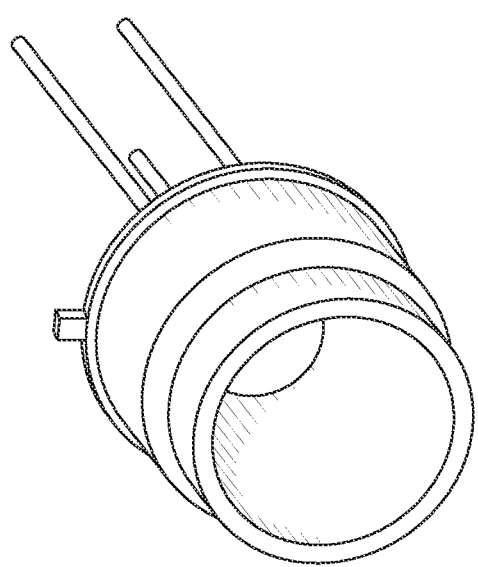

COLLABORATIVE SENSING AND PREDICTION OF SOURCE ROCK PROPERTIES

CROSS-REFERENCE TO RELATED APPLICATIONS

This application claims the benefit of U.S. Provisional Application No. 62/471,274, filed Mar. 14, 2017, which is incorporated herein by reference in its entirety.

FIELD

Disclosed here are methods, apparatuses, and systems generally directed to the sensing and prediction of the properties of source rock.

BACKGROUND

In conventional reservoirs, oil and gas is recovered from stratigraphic or structural traps in sandstone or limestone. The hydrocarbons migrate and collect in these reservoirs after being generated from some deeper source rock in the basin. In unconventional reservoirs, a source rock serves both as the source and reservoir within the rock fabric. The value of the hydrocarbons extracted from each type is highly dependent on the properties of the source rock associated with each. Understanding, predicting and explaining the properties of the hydrocarbons produced by each type of reservoir requires the analysis of the source rock using a myriad of methods to confirm maturity and type. Maturity and source rock type are parameters that have the greatest effect on the fluid properties of the hydrocarbon generated, such as Gas/Oil Ratio (GOR), gas wetness or dryness, and viscosity all of which influences its mobility and quality. For example, successful oil and gas production in unconventional reservoirs is dominated by condensate/gas mixtures. This is primarily related to Type II marine source rocks. These source rocks have been transformed during late oil maturity phase where the maximum intra-kerogen porosity develops as a result of this maturity cycle. The reservoir pressures generated during this maturity cycle are caused by oil to gas cracking, which provides the gas drive needed for expulsion of the hydrocarbon generated. This internal pressure results in greater gas storage capacity, which can be exploited through hydraulic fracking to fracture the rock and recover the hydrocarbon. The fluid produced is a very light crude of low viscosity and high GOR containing large volumes of wet gas. The wet gas is more easily refined into a valuable product. In contrast, conventional reservoirs contain heavier density petroleum, which has migrated from less mature source types. These reservoirs can present costly production challenges during recovery as the high viscosity and low GOR reduces mobility of the fluid in the reservoir. Refining this type of petroleum is also costly due to removal of excess resins and asphaltenes and the need for cracking heavier hydrocarbons in refining processes, thus reducing the net value of the product finally produced.

Commercial exploitation depends on identification of effective source rock that contains the desired organofacies profile and desired maturity and is presently generating or has the capacity to produce hydrocarbons. Therefore, mineralogical and organic geochemical information on reservoir and source rocks is critical for assessment and optimal production of hydrocarbons. The standard methods of obtaining source-rock properties are via bulk measurements on homogenized, crushed/pulverized samples. Pulverized rock is subject to extraction processes that separate the organic components of the rock sample. The extracted organic components are analyzed to determine the maturity and organofacies profile of the source rock sample.

SUMMARY

Several risks were recognized in the assessment of extracted and pulverized source rock samples. These risks include, but are not limited to, alteration of the extracted components during the analysis and contamination of the analysis by components from the extraction processes. Moreover, samples are taken from the reservoir and analyzed later at the surface or taken to laboratories and analyzed much later. This process can take a long time, and the information is not available in time to inform completion decisions about the well where it is collected. This process is also expensive, so mineralogy and maturity information is collected occasionally and at a few selected sample locations. Significant information about the rocks may be missed due to this limited sampling. Accordingly, there is a need for a wireline logging tool and other data acquisition devices that can provide information within hours about mineralogy and maturity in the reservoir interval and can obtain a full profile of properties along the well instead of a small set of measurements at select locations. A need was also recognized for a cased hole logging tool, which can measure properties of the produced fluids, as these properties change over time during production to indicate the connectivity of the reservoir and whether there may be bypassed oil.

Spectroscopy measurements involve a light source, the reflection of the light off or transmission of the light through a sample, and the detection of the light intensity by a detector. In addition, the source is monochromatic or the detector is made wavelength selective so that the attenuation of the light (whether by reflection or transmission) may be observed as a function of wavelength. Current laboratory spectroscopy instruments for medium and long infrared (IR) wavelengths generally use semiconductor photodiode detectors. These detectors are made of materials such as mercury cadmium telluride, indium gallium arsenide, or indium arsenide, all of which must be cooled below ambient temperatures (for example, thermoelectrically or with liquid nitrogen) to achieve useable signal-to-noise ratios.

In certain embodiments, these detectors are replaced with other kinds of detectors to enable rapid spectroscopy measurements with suitably sized components to use in a wireline tool and can operate at downhole temperatures. It was further recognized that the determination of the composition of reservoir rocks and fluids could be made with a small subset of wavelengths—a full spectrum may not be necessary. So, the downhole spectrometer can be designed to provide absorption at a handful of selected wavelengths. As only a few wavelengths are needed, longer observation times at each wavelength are possible using this data acquisition device, allowing time to average out the higher noise levels produced by the high downhole temperatures. An embodiment of a downhole spectrometer includes at least a light source, a detector, a component to reflect light from the material of interest (whether fluid or rock) and direct reflected light to the detector, components to deploy the source and detector into a well, and components to retrieve data obtained in the spectral measurement.

Disclosed here are embodiments of systems, computer-implemented methods, and a non-transitory, computer-readable medium having stored computer programs. These embodiments are directed to address the shortcomings of the art, including specific methods for spectral and optical measurements of the source rock sample to determine its properties via sensing devices and specialized algorithms. These methods and systems provide spatially accurate and timely characterization that is vital to exploration, development and reservoir production.

The disclosure here provides for a computer implemented methods of determining maturity of a sample source rock. One such method includes the step of establishing, by a data analysis engine, communication links with a source rock database and a plurality of data acquisition devices placed in vicinity of a sample source rock. The source rock database contains a first plurality of data acquired from a plurality of representative source rocks and a plurality of properties of the plurality of representative source rocks. The method further includes the steps of acquiring, by the data analysis engine, a second plurality of data of a sample source rock from the plurality of data acquisition devices; and analyzing, by the data analysis engine, the second plurality of data using a predictive correlation to determine maturity of the sample source rock. The predictive correlation is generated by the data analysis engine by applying a machine learning model to correlate the first plurality of data acquired from a plurality of representative source rocks with the plurality of properties of the plurality of representative source rocks. The plurality of data acquisition devices can include a spectrometer with a light source, a pyroelectric detector, and a component to reflect light from the sample source rock and direct reflected light to the pyroelectric detector. The pyroelectric detector can be integrated with a tunable filter. In certain embodiments, the component to reflect light from the sample source rock and direct reflected light to the pyroelectric detector is an attenuated total reflectance unit. In certain embodiments, the method can further include the steps of preparing the second plurality of data before the step of analyzing the second plurality of data by the data analysis engine by implementation of one or more of outlier detection, baseline correction, peak enhancement, and normalization. The method further includes the steps of storing, by the data analysis engine, the first plurality of data of a sample source rock and the determined maturity of the sample source rock in a source rock database. The properties of the plurality of representative source rocks can include kerogen typing and elemental compositions. The first plurality of data can include two or more of location data, spectral measurements, and optical measurements acquired from the plurality of representative source rocks. The spectral measurements can include one or more of measurements obtained from Fourier Transform Infrared spectroscopy (FTIR), Electron Spin Resonance spectroscopy (ESR), terahertz spectroscopy (THz), and Ultraviolet (UV) spectroscopy. In certain embodiments, the first plurality of data further includes pyrolysis data. The pyrolysis data can be obtained by Rock-Eval® pyrolysis analysis of the plurality of representative source rocks. In certain embodiments, the second plurality of data includes two or more of location data, spectral measurements, and optical measurements acquired from the sample source rock. The spectral measurements can include one or more of measurements obtained from Fourier Transform Infrared spectroscopy, Electron Spin Resonance spectroscopy, terahertz spectroscopy, and Ultraviolet spectroscopy. The optical measurements can include one or more of measurements obtained by fluorescence microscopy and confocal laser scanning microscopy. Certain embodiments include a machine learning model based on one or more of support vector machine, Random Forest®, logistic regression, and Adaptive Boosting algorithms. Certain embodiments of the method further include the step of selecting a spectroscopic wavenumber band for operation of the plurality of data acquisition devices in vicinity of the sample source rock. The spectroscopic wavenumber band for the sample source rock can be selected in response to receiving, by the data analysis engine, one or more selections of desired maturity and desired organofacies profile of the sample source rock from a user interface.

Embodiments include systems to determine maturity of a sample source rock. One such system includes a plurality of data acquisition devices placed in vicinity of a sample source rock and communicatively coupled to a computing device. The computing device is coupled to a source rock database via a communication network. The computing device is configured to obtain a first plurality of data of a sample source rock from the plurality of data acquisition devices; and analyze the first plurality of data using a predictive correlation to determine maturity of the sample source rock. The source rock database contains a second plurality of data associated with a plurality of representative source rocks, a plurality of properties of the plurality of representative source rocks, and a predictive correlation that is generated by applying a machine learning model to correlate a second plurality of data acquired from a plurality of representative source rocks with a plurality of properties of the plurality of representative source rocks. The plurality of data acquisition devices can be positioned to acquire data from optimal sensing bands of the sample source rock. The system can further include a sample source rock retrieving apparatus to obtain a portion of the sample source rock. The plurality of data acquisition devices can be positioned to acquire two or more of location data, spectral measurements, and optical measurements. The spectral measurements can include one or more of measurements obtained from Fourier Transform Infrared spectroscopy, Electron Spin Resonance spectroscopy, terahertz spectroscopy, and Ultraviolet spectroscopy. The optical measurements can include one or more of measurements obtained by fluorescence microscopy and confocal laser scanning microscopy. The data acquisition devices can include a spectrometer comprising a light source, a pyroelectric detector, and a component to reflect light from the sample source rock and direct reflected light to the pyroelectric detector. The pyroelectric detector can be integrated with a tunable filter. The component to reflect light from the sample source rock and direct reflected light to the pyroelectric detector can be an attenuated total reflectance unit.

Another system to determine maturity of a sample source rock includes a gas-in-place data acquisition device placed in vicinity of a sample source rock and communicatively coupled to a computing device. The computing device is coupled to a source rock database via a communication network and configured to obtain a first plurality of data of a sample source rock from the gas-in-place data acquisition device and analyze the first plurality of data using a predictive correlation to determine maturity of the sample source rock. The source rock database contains a second plurality of data associated with a plurality of representative source rocks, a plurality of properties of the plurality of representative source rocks, and a predictive correlation generated by applying a machine learning model to correlate the second plurality of data acquired from the plurality of representative source rocks with the plurality of properties of the plurality of representative source rocks. The gas-in-place data acquisition device can include a spectrometer comprising a light source, a pyroelectric detector, a gas inlet, a gas outlet, and a sample chamber. In certain embodiment, the gas-in-place data acquisition device is deployed as part of a logging while drilling assembly. In certain embodiment, the gas-in-place data acquisition device is deployed as part of a wireline logging assembly.

Numerous other aspects, features and benefits of the present disclosure may be made apparent from the following detailed description taken together with the drawing figures. The systems can include less components, more components, or different components depending on desired analysis goals.

BRIEF DESCRIPTION OF THE DRAWINGS

While this disclosure is susceptible to various modifications and alternative forms, specific embodiments are shown by way of example in the drawings and will be described in detail here. The drawings may not be to scale. It should be understood, however, that the drawings and the detailed descriptions thereto are not intended to limit the disclosure to the particular form disclosed, but, to the contrary, the intention is to cover all modifications, equivalents, and alternatives falling within the spirit and scope of the present disclosure as defined by the appended claims.

FIGS. 20A and 20B present the evaluation results in the form of confusion matrix following classification of source rock samples using two different machine learning algorithms—Adaptive Boosting (shown in FIG. 20A) and Random Forest® methods (shown in FIG. 20B).

FIG. 21 represents the maturity index (the ratio of Hydrogen Index (HI) to Vitrinite Reflectance (Ro %)) as predicted from FTIR spectra of source rock samples by two different machine learning algorithms—Adaptive Boosting and Random Forest® methods as compared to the maturity index obtained by conventional methods of processing the various source rocks.

FIG. 22A represents a simplified thermal model and FIG. 22B represents the equivalent electrical circuit of a pyroelectric detector, according to an embodiment.

FIG. 26 is a diagrammatic representation of a GIP data acquisition device using a pyroelectric sensor, according to an embodiment.

FIGS. 27A, 27B, and 27C are photographs of laboratory prototypes of the GIP data acquisition device, a light source, and a pyroelectric detector, respectively, according to an embodiment.

DETAILED DESCRIPTION

Figure 1:
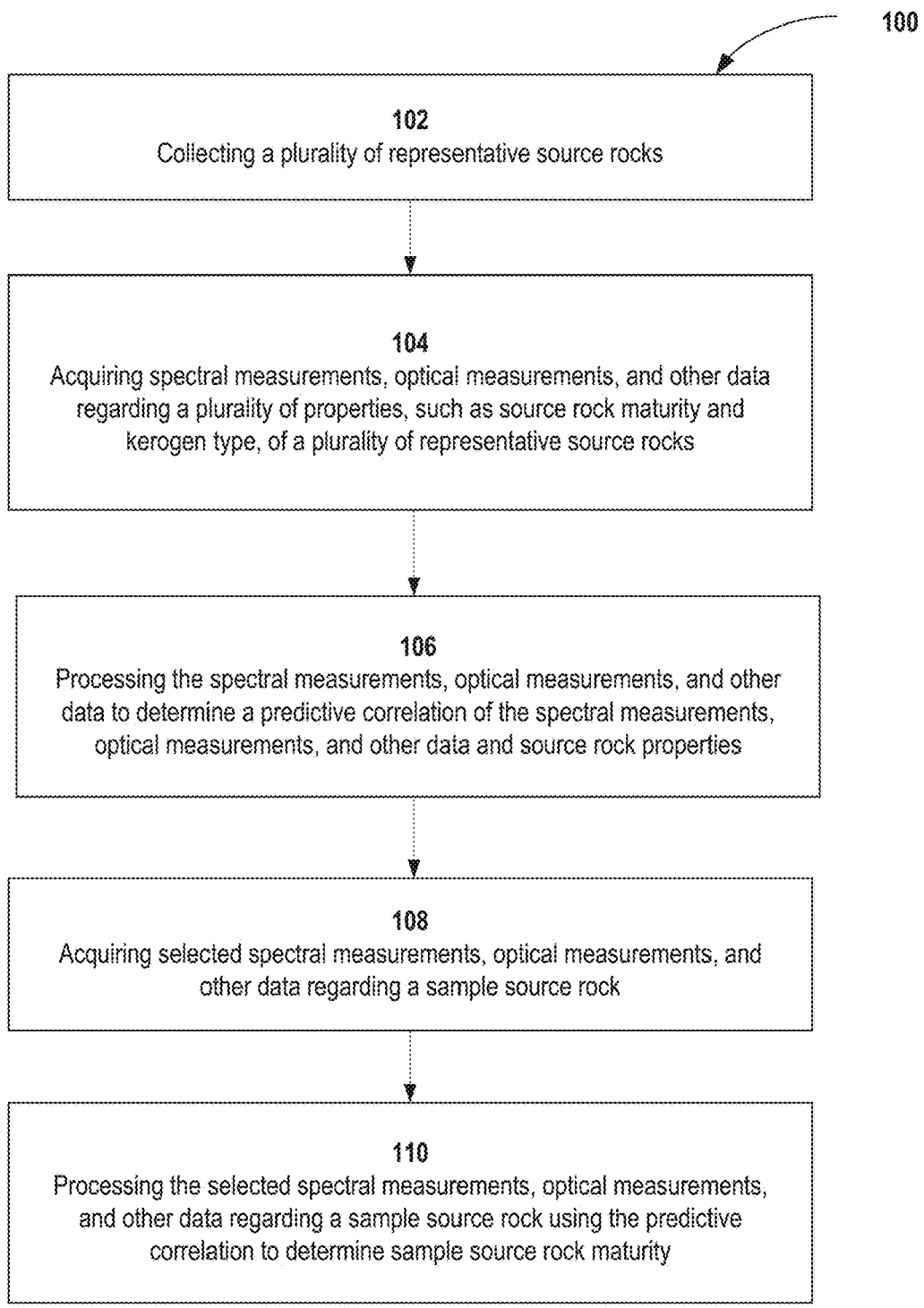
FIG. 1 is a flowchart illustrating a method for determining certain properties of a source rock sample, according to an embodiment.

In the following description, numerous specific details are set forth in order to provide a thorough understanding of the various embodiments. In other instances, well-known processes and methods may not be described in particular detail in order not to unnecessarily obscure the embodiments described here. Additionally, illustrations of embodiments here may omit certain features or details in order to not obscure the embodiments described here.

In the following detailed description, reference is made to the accompanying drawings that form a part of the specification. Other embodiments may be utilized, and logical changes may be made without departing from the scope of the disclosure. Therefore, the following detailed description is not to be taken in a limiting sense.

The description may use the phrases "in some embodiments," "in various embodiments," "in certain embodiment," or "in embodiments," which may each refer to one or more of the same or different embodiments. Furthermore, the terms "comprising," "including," "having," and the like, as used with respect to embodiments of the present disclosure, are synonymous.

The success of exploiting and extracting the hydrocarbons of greatest value requires an understanding of the source rocks within a given basin both for unconventional and conventional reservoirs. Systems and methods provide for high grading of target source rocks that requires development of an intelligent system involving machine learning and chemometric methods. In this framework, all the analytical data used to determine maturity and source type are integrated and analyzed to arrive at determinations of concerning maturity and source. This system can be used to predict probable API gravity, Gas oil ratio, and viscosity of the hydrocarbons, and then estimate the cost of extracting, producing, and refining the targeted hydrocarbons, and also provide uncertainty quantification for these predicted values.

As used here, the term "source rock" refers to a rock that is capable of generating or that has generated movable quantities of hydrocarbons. A large number of representative source rock samples, their locations such as the variety of well sites, their organofacies profile, their age and maturity, spectral measurements, and other measurements of the representative source rocks are recorded in the database and used to develop a correlation of spectral measurements to source rock properties.

A "data analysis engine" refers to one or more software modules that handle data, formulate models and rules, and perform data matching, training and cross-validation by using appropriate logic and criteria, including but not limited to software for the prediction of the properties of source rock. In some embodiments, the data analysis engine can be implemented as part of a server, a user computing device and the like. Examples of suitable implementations of the data analysis engine include servers, authorized user computing devices, smartphones, desktop computers, laptop computers, tablet computers, PDAs and other types of processor-controlled devices that receive, process, or transmit digital data.

Characterization of mineral content and organic matter maturity in rocks is important for determining the optimal depth for laterals in shale reservoirs, the optimal location for hydraulic fracturing of wells in shale reservoirs, and for refining basin models and geological understanding of hydrocarbon systems. In shale reservoirs, the maturity and amount of organic material can indicate the kerogen porosity and the gas in place. When materials are past a certain maturity level, the porosity may collapse and the gas may not be present. Mineralogy indicates how effectively the shale can be fractured. Characterization of the composition of produced fluids can indicate the physical properties of the fluids, which can be important for designing well completions, artificial lift, and surface facilities. Differences in fluid composition between two producing zones or between two wells can indicate that the zones or wells are not in communication. It can also indicate that the respective fluids came from different source rocks or had different temperature, biodegradation, or other alterations after emplacement.

Certain aspects of the disclosure include methods, systems, and software products for prediction of the properties of source rock based on spectral measurements and optical measurements. Certain embodiments include specific methods, systems, and software products include integration of multiple measurements of source rock samples using spectroscopic and optical measurement and sensing technologies for geochemical and mineralogy characterization of source rock, such as classification of the source rock based on its maturity and organofacies profile.

Methods, systems, and software products in this disclosure relate to technologies for determining selected source rock properties based upon selected spectral measurements. Also included here is a database of source rock properties that is utilized to generate a predictive correlation of the spectral measurements to the selected source rock properties. The source rock database is a database containing measurements of several characteristics of a large number of source rock samples representative of different maturity level and depositional origin. The database includes measurements on representative source rocks, such as selected spectral measurements, optical measurements, and standard measurements of source rock properties. These properties include the maturity of a source rock and the type of kerogen present in the source rock. The spectral measurements, optical measurements, and standard measurements are processed using computer algorithms to develop correlations of select aspects of the spectral measurements to the properties of source rock. The correlations developed between the spectral measurements and the properties of source rock are used to predict source rock properties of an unknown source rock based on the spectral and optical measurements on the source rock.

The source rock database can be configured as a combination of external sources and internal databases, and is implemented as object-oriented, network, or semi-structured or other flexible database or combinations thereof to provide functions of fetching, indexing, and storing data. In these embodiments, the source rock database provides data and other stored data and files to one or more software modules in the system. External data sources can be, for example, a single database, multiple databases, or a virtual database, including data from multiple sources, for example, servers on the World Wide Web. In these embodiments, the source rock database can be implemented using application protocols for accessing and maintaining spectral measurements, optical measurements, and standard measurements of representative source rocks, among others. It will be appreciated by those having skill in the art that data described in this disclosure as being stored in the databases can also be stored or maintained in non-transitory memory and accessed among subroutines, functions, modules, objects, program products, or processes, for example, according to objects or variables of such subroutines, functions, modules, objects, program products or processes.

Certain embodiments of the methods, systems, and software products in this disclosure relate to a novel sensing technology directed to only a subset of wavenumber bands that bear significance to the maturity, kerogen type and other geologic properties (such as organofacies). Based on a spectra database consisting of a large number of representative samples and several spectral measurement types, several novel algorithms have been developed to identify the information overlaps and gaps among several different measurements such as FTIR, Florescence, THz, and ESR data. This was achieved through collaborative learning of algorithms applied to multiple spectral measurements, specifically with high-dimensional feature learning, classification and prediction algorithms. The optimal sensing bands and predictors were derived as the solution to a constrained optimization problem, which maximizes the total information relevant to the source rock properties (maturity and kerogen type) under field accessible constraints.

When an unknown source rock sample has to be characterized, the spectral measurements are performed on whole rock samples and correlated to source rock properties obtained from testing of source rock samples. In certain embodiments, the source rock properties of the unknown sample are determined based on spectroscopy measurements alone on the whole rock portion of the unknown sample. In certain embodiments, the measurements are made at the site of the source rock. These embodiments provide cost-effective and reliable multi-spectral in-situ sensing, accurate prediction of source rock maturity and organofacies profile, accurate reserve and productivity estimation, which lead to increased production of hydrocarbons, optimized recovery methods, and greater risk mitigation.

In certain embodiments, the computer implemented method of determining properties of sample source rocks includes the following steps performed by a data analysis engine: obtaining a first plurality of data of a sample source rock from a plurality of data acquisition devices placed in vicinity of the sample source rock and analyzing the received data using a predictive correlation to determine maturity of the sample source rock. The received data is processed by implementing outlier detection, baseline correction, peak enhancement, and normalization before being subject to analysis by the data analysis engine. The predictive correlation is generated by the data analysis engine by applying a machine learning model to correlate data acquired from a plurality of representative source rocks with a plurality of properties of the plurality of representative source rocks. The source rock database stores data acquired from the plurality of representative source rocks, the properties of various representative source rocks, the received data of the sample source rock, and the determined maturity of the sample source rock.

In certain embodiments, the computer implemented method of determining maturity of a sample source rock can include selecting a spectroscopic wavenumber band for operation of the plurality of data acquisition devices in vicinity of the sample source rock. The spectroscopic wavenumber band for the sample source rock is selected responsive to receiving one or more selections of desired maturity and desired organofacies profile of the sample source rock from a user interface.

In certain embodiments, the spectroscopic technologies include one or more of FTIR, THz, ESR, and fluorescence spectroscopy. Examples of properties that are tested include vitrinite reflectance, hydrocarbon index, elemental composition, pyrolysis, and lipinite fluorescence. These tests provide an indication of source rock maturity and kerogen type. Further analytical methods such as high performance liquid chromatography (HPLC), gas chromatography (GC), and GC mass spectrometry (GC-MS) can be used for characterizing the kerogen of representative source rock samples. A set of optimal sensing attributes are derived for the purpose of in situ field sensing and prediction such as sub-bands of the various spectroscopy measurements. In certain embodiments, the rock samples are evaluated using one or more of FTIR spectroscopy, fluorescence spectroscopy, THz spectroscopy, ESR spectroscopy, energy dispersive X-Ray (EDS or EDX) spectroscopy. Rock Samples are also evaluated using Rock-Eval® pyrolysis.

Embodiments disclosed here also include a computer system, associated with the data acquisition devices, which includes a memory, a processor, and one or more input/output (I/O) interfaces. The memory can include non-volatile memory (for example, flash memory, read-only memory (ROM), programmable read-only memory (PROM), erasable programmable read-only memory (EPROM), electrically erasable programmable read-only memory (EEPROM)), volatile memory (for example, random access memory (RAM), static random access memory (SRAM), synchronous dynamic RAM (SDRAM)), bulk storage memory (for example, CD-ROM, DVD-ROM, or hard drives), and combinations thereof. The memory can include a non-transitory computer-readable storage medium having program instructions stored therein. The program instructions can include program modules that are executable by a computer processor to cause the functional operations described here, including those described with regard to determining the maturity of source rock samples.

The processor can be any suitable processor capable of executing/performing program instructions. The processor can include a central processing unit (CPU) that carries out program instructions (for example, the program instructions for the methods shown in FIGS. 1, 2, 3, and 13) to perform the arithmetical, logical, and input/output operations described here. The processor can include one or more processors. The processor can be communicatively linked to one or more I/O devices, such as a joystick, a computer mouse, a keyboard, a display screen (for example, an electronic display for displaying a graphical user interface (GUI)), a touch or voice responsive device, and the like. The I/O devices can include one or more of the user input devices, one or more data acquisition devices, one or more data processing instruments, and combinations thereof. These devices can be connected to the processor and the I/O interfaces via a wired or a wireless connection. The I/O interface can provide an interface for communication with one or more external devices, such as other computers, networks, data acquisition devices, sampling devices, and combinations thereof. In some embodiments, the I/O interface includes an antenna, a transceiver, and other components required to be communicatively coupled to the other devices. In some embodiments, the external devices include an upstream facility. The various illustrative logical blocks, modules, circuits, and algorithm steps described in connection with the embodiments disclosed here can be implemented as electronic hardware, computer software, or combinations of both. A communication link is established among two or more devices in this system when these devices are enabled to exchange data, control signals, or other information among them. To clearly illustrate this interchangeability of hardware and software, various illustrative components, blocks, modules, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosure.

FIG. 1 is a flowchart illustrating a method 100 for determining certain properties of a source rock sample, according to an embodiment. A large set of representative source rocks are collected at step 102. The data analysis engine acquires spectral measurements, optical measurements, and other data regarding a plurality of properties, such as source rock maturity and kerogen type, of the representative source rocks at step 104. The data analysis engine processes spectral measurements, optical measurements, and other data to determine a predictive correlation between the spectral measurements, optical measurements, and other data and the source rock properties, at step 106. The data analysis engine acquires selected spectral measurements, optical measurements, and other data regarding a sample source rock, at step 108. The data analysis engine processes the selected spectral measurements, optical measurements, and other data regarding a sample source rock using the predictive correlation to determine sample source rock maturity, at step 110.

Figure 2:
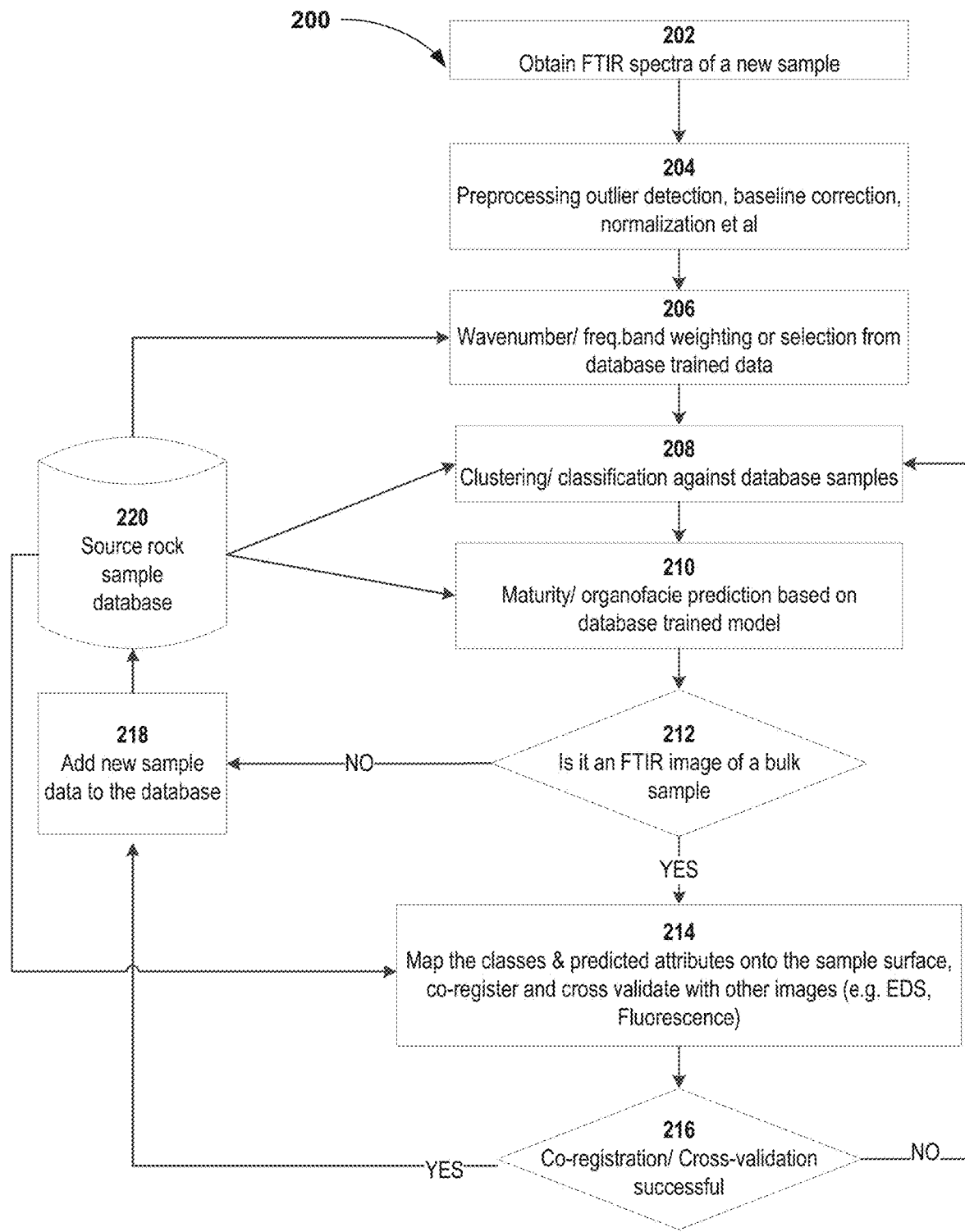
FIG. 2 is a flowchart illustrating a method for determining certain properties of a source rock sample, according to another embodiment.

FIG. 2 is a flowchart illustrating a method 200 for determining certain properties of a source rock sample, according to an embodiment. The FTIR spectra of a new sample is obtained at step 202. The FTIR spectra is subject to preprocessing methods, such as outlier detection, baseline correction, and normalization at step 204. The wavenumber/frequency bands are selected by weighting or selected from the source rock database trained data at step 206. The processed FTIR spectra is subject to clustering or classification against database samples at step 208. The maturity/organofacies profile is predicted based on source rock database trained models at step 210. If the FTIR image is of a bulk sample at step 212, then classes and predicted attributes are mapped onto the sample surface, and co-registered and cross-validated with other images, such as energy dispersive X-Ray spectroscopy (EDS or EDX) or fluorescence at step 214. If co-registration/cross-validation is successful at step 216, then the new sample and all the acquired data and analysis are added to the source rock database 220 at step 218. If the FTIR image is not that of a bulk sample at step 212, then the data from the source rock sample is added to the source rock database 220 at step 218. If co-registration/cross-validation is not successful at step 216, then the process is repeated from step 208.

Figure 3:
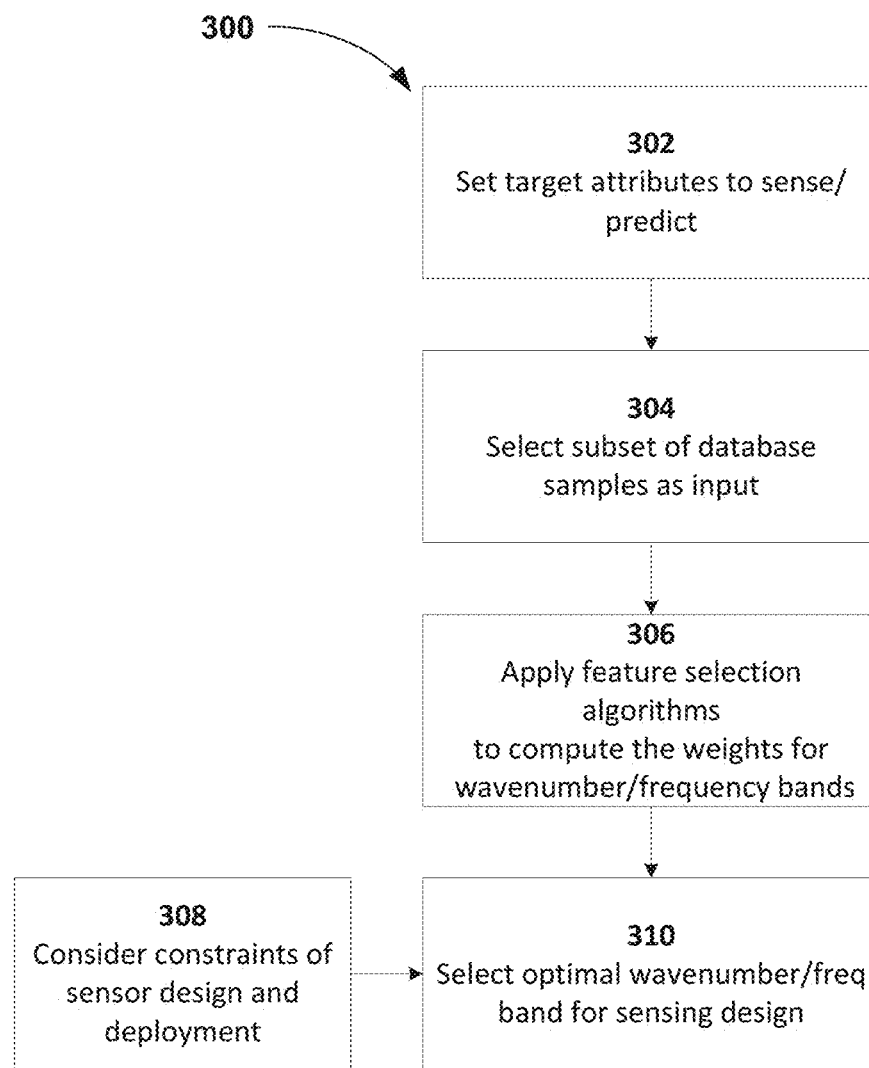
FIG. 3 is a flowchart illustrating a method for selecting spectroscopic wavenumber bands for operation of the plurality of data acquisition devices in vicinity of the sample source rock, according to another embodiment.

FIG. 3 is a flowchart illustrating a method 300 for determining certain properties of a source rock sample, according to an embodiment. At step 302, target attributes such as maturity and organofacies profile are set to sense or predict properties of a source rock sample. At step 304, a subset of database samples is selected from the curated source rock database as input. At step 306, feature selection algorithms are utilized to compute the weights for wavenumber/frequency bands from the selected database samples. At step 308, feasibility constraints of sensor design and deployment are considered in selection of optimal wavenumber/frequency bands. At step 310, these bands are selected through feature ranking and serve as sensing bands. These sensing bands are most informative to the chosen target attributes, or contribute most to distinguish differences in the source rock sample.

Certain embodiments include an apparatus to perform the selected spectral measurements in selected sub-bands in a borehole and communicate the spectra to a surface computer for processing or possibly performing the processing itself and communicating the results of maturity and kerogen type. A set of methods has been developed for predicting source rock properties (maturity and organofacies) from multiple measurements in general and selected sensing, and in certain embodiments, these multiple measurements are from in-situ field sensing. Rock mineralogical and organic geochemical information on reservoir and source rocks, important for assessing and producing petroleum systems, are inferred from several types of spectroscopic measurements, such as FTIR, ESR, THz, and UV spectroscopy, gas chromatography (GC), and mass spectrometry (MS). A database is constructed consisting of these measurements taken from a collection of representative source rock samples. Source rock classification of new or unknown samples are determined by leveraging the database. Optimal attributes for predicting source rock maturity and organofacies types are derived from all or a subset of these measurements, and compared with indices such as vitrinite reflectance and hydrocarbon index. The behavior of molecular structures and changes induced by varying maturity levels are also compared to values in the database. A set of optimal sensing attributes are derived for the purpose of in-situ field sensing and prediction. Spectroscopic wavenumber bands that strongly correlate with the optimal attributes are identified, including those from different types of physical measurements and the different sub-bands of each type of measurements. This provides guidelines for selection of bands for in-situ sensing in field applications. The selected sensing bands and their accuracy and certainty in predicting maturity and organofacies types are also quantified. This is achieved using the optimal attributes based on available spectral inspection data for the unknown sample, or the attributes derived from the in-situ selected sensing band data.

An attribute of the source rock maturation process is the physical and chemical transformation of kerogen structure through thermogenic processes induced by burial of the source rock. The ensuing temperature gradient causes thermal decomposition of kerogen into hydrocarbons. Normally, the progression of this maturity is measured by a number of different time-intensive methods such as elemental composition, pyrolysis, vitrinite reflectance, and liptinite fluorescence. Vitrinite reflectance (% Ro) is a visual microscopic estimate of the reflectance of light from the vitrinite maceral in kerogen. With suitable calibration, the range of reflectance values can reflect the maturity of source rocks. An example of the ranges of vitrinite reflectance (% Ro) values indicative of the age of source rocks is provided in Table 1. These reflectance value windows can vary between different source rocks and with different kerogens.

TABLE 1

| Reflectance Value | Age of the source rock |
| --- | --- |
| 0.25-0.6 | Immature |
| 0.6-0.8 | Early Maturity |
| 0.8-1.1 | Peak Maturity |
| 1.1-1.35 | Late Maturity |
| 1.35> | Dry Gas - Over mature |

Measurement of elemental composition of source rocks aids determination of kerogen maturity and is presented as loss of hydrogen relative to carbon and oxygen as measured from the concentration of those elements. The systematic decline in hydrogen to carbon ratio relative to the oxygen to carbon ratio as plotted on a compositional diagram, known as a Van Krevelen diagram, provides an estimate of maturity. Moreover, the behavior of H/C ratio relative to O/C ratio also provides an estimate of maceral composition in kerogen and whether immature source rocks are classified as a type I, II, III, or IV. These four types are based on the relative amounts of carbon, hydrogen, and oxygen present in the source rock samples. As oil and gas are generated in the source rock, the kerogen becomes depleted in hydrogen and oxygen relative to carbon. The hydrogen content in kerogen is proportional to the oil-generative potential of the source rock.

Attributes and classification of source rocks are related to organofacies that reflects both the type of organic matter and the composition of sediments related to the depositional environment. This is defined based on relative abundance of maceral type and the provenance of the sediment composing the matrix. Macerals are blueprint remnants of preserved algal and plant debris and contain organic matter, which include three main types: Liptinite, Vitrinite and Inertinite. These organofacies are diagnostic and provide insight into potential hydrocarbon productivity and fluid quality that are expected from certain source rock organofacies. For example, a Type II-S carbonate organofacies (sulfur-rich kerogen) contains liptinite macerals, which are highly volatile and will produce oil. Oil maturity, however, will be reached at a much lower temperature compared to that of a standard Type II kerogen, which also contains volatile liptinite macerals and produces oil. This occurs because of a lower activation energy that is linked to sulfur, which serves as a free radical for increasing reactivity. A Type III siliceous organofacies in contrast will tend to produce more gas, because the kerogen composition is less volatile and has a lower H/C ratio due to the abundance of vitrinite. Type IV organofacies, dominated by inertinite, are the least volatile with even still lower H/C and have no hydrocarbon generative potential. Thus, it is not considered an attractive hydrocarbon source rock. These are just a few of the types of organofacies that are encountered in the rock record of various basins.

A large set of source rock samples has been collected from various well-sites, subject to all or a selected set of measurements described here. In addition to these spectroscopic and optic measurements, the samples also have other associated data, including but not limited to the sample location, depth, Rock-Eval® analytical results, FTIR spectral measurement and images, elemental composition maps, confocal fluorescence images, X-ray fluorescence images, ESR measurements, THz images, and other data. Rock-Eval® pyrolysis, a widely-used technique developed by the Institut Français du Pétrole, is used to measure the quantity, quality, and thermal maturity of organic matter in rock samples, and includes determination of hydrocarbon-generation potential, organic character, and the extent of thermal diagenesis (maturation). The FTIR data includes raw as well as preprocessed spectra, FTIR imaging data, and FTIR spectra of extracted samples. A FTIR spectrum typically needs to be preprocessed to remove baseline, suppress noises, and normalize the spectrum, before further analysis such as clustering, classification, prediction and interpretation are performed. The input spectra and the output spectra of these preprocessing steps is referred to as the raw and the preprocessed spectra, respectively. Elemental composition data includes individual mineral maps and mineral distribution of the source rock samples, and is obtained using techniques, such as chemical microanalysis based on EDS.

Figures 4A, 4B:
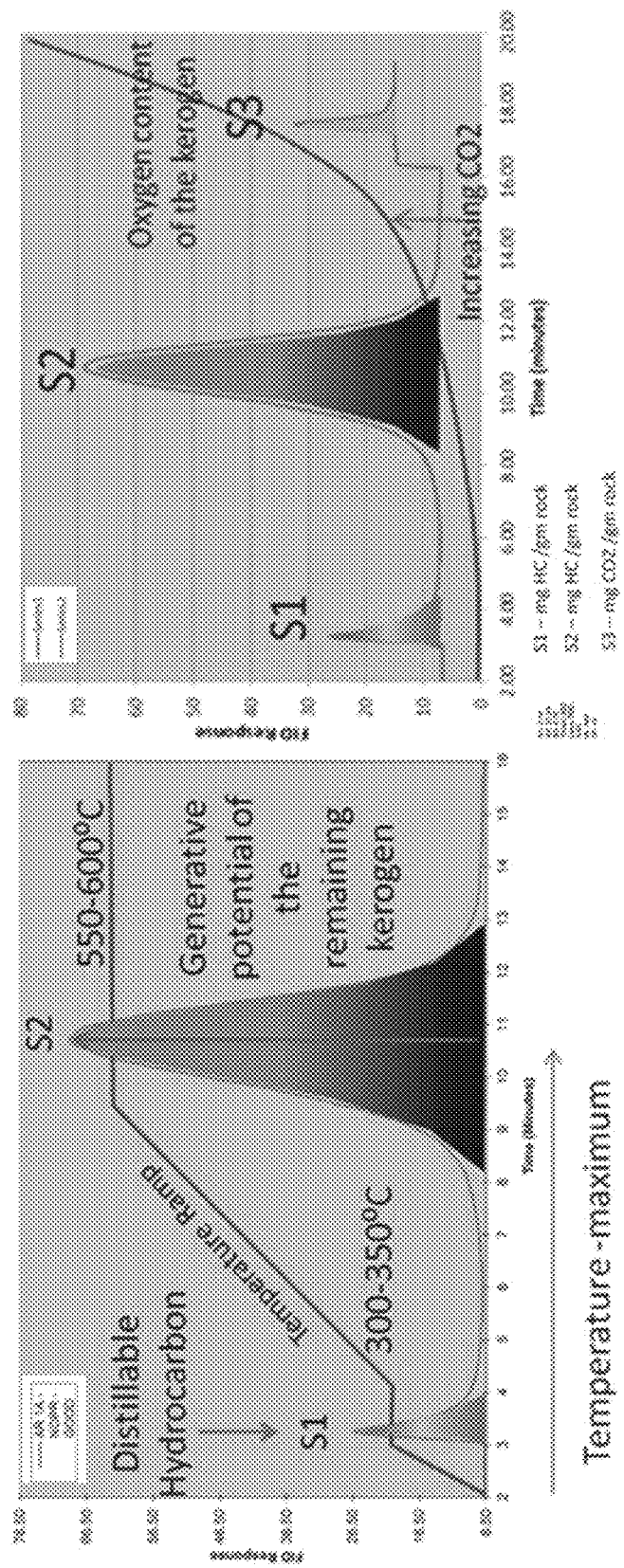
FIGS. 4A and 4B are sample programs showing data obtained from pyrolysis of two representative source rock samples.

FIGS. 4A and 4B are sample pyrograms showing Rock-Eval® data obtained from an immature Silurian Type II kerogen source rock sample, such as Sample 3A in Table 2. Peaks in the pyrograms represent the mobile and immobile hydrocarbon fractions in a source rock and are recorded as pyrolysis data (S1 & S2 values). These values are used to calculate maturation indices. The S1 peak represent mobile, distillable hydrocarbons or bitumen that are released from kerogen at a temperature of 330° C. while S2 values represents the remaining generative potential of the kerogen which evolves at 550-600° C. Both the S1 and S2 values are recorded as milligrams per gram of rock. The S3 peak corresponds to carbon dioxide that is produced from thermal cracking of kerogen, and is also recorded in milligrams per gram of source rock. The Tmax value is the maximum temperature reached for the S2 value and provides some measure of maturity of the source rock. Table 2 is a listing of source rock samples used in this study as well as their Rock-Eval® parameters and recorded pyrolysis data. These samples are all Silurian aged, Type-II kerogen source rock samples from different locations and depths across a single geologic basin. The samples, therefore, have undergone different maturation histories due to differences in geographic location and burial depths. These samples were chosen to provide a wide range of hydrocarbon maturities ranging from immature to peak gas generation.

Table 2 is a listing of a few source rock examples and their Rock-Eval® parameters. These are representative of Type-II Silurian aged source rocks that cover a range of maturity from early oil to gas maturity. The S2 value divided by total organic carbon (TOC) provides a hydrogen index (HI) that can be used to estimate maturity (% Ro-HI), especially when the T-max is not easily resolvable from the program. The unresolved T-max (N/A value) occurs with over-mature samples such as the Samples 4A and 4D samples where the generative potential has been depleted as is seen by the low S2 value which equates to low HI-% Ro (2.0-2.5) characteristic of gas maturity. Likewise, the Type-II Samples 3A, 3B, and 3C represent samples in early oil window as can be seen by the HI-% Ro of 0.62-0.64. In turn, "peak oil" maturity is characteristic of the Sample 1A (HI-% Ro=1.02) and final condensate maturity for Sample 2A (HI-% Ro=1.59).

TABLE 2

| Samples | Depth(ft) | S1 (mg/g) | S2 (mg/g) | Tmax (° C.) | HI | OI | PI | TOC (%) | % Ro-Tmax | HI-% Ro | HC Window |
|---|---|---|---|---|---|---|---|---|---|---|---|
| 1A | 13,500 | 2.64 | 9.85 | 439 | 185 | 3 | 0.21 | 5.33 | 0.74 | 1.02 | Peak Oil |
| 2A | 15,100 | 1.49 | 1.73 | 456 | 45 | 3 | 0.46 | 3.87 | 1.05 | 1.59 | Late Oil |
| 3A | 6,300 | 2.14 | 27.24 | 422 | 485 | 12 | 0.07 | 5.62 | 0.44 | 0.63 | Immature |
| 3B | 6,300 | 2.2 | 29.31 | 422 | 476 | 9 | 0.07 | 6.16 | 0.44 | 0.64 | Immature |
| 3C | 6,300 | 2.82 | 35.4 | 421 | 504 | 8 | 0.07 | 7.02 | 0.42 | 0.62 | Immature |
| 4A | 6,500 | 0.08 | 0.09 | N/A | 4.21 | 0.93 | 0.47 | 2.14 | N/A | 2.54 | Gas |
| 4B | 6,500 | 0.16 | 1.07 | 523 | 8.36 | 1.09 | 0.13 | 12.8 | 2.25 | 2.26 | Gas |
| 4C | 6,600 | 0.09 | 0.31 | 534 | 10.84 | 0.35 | 0.23 | 2.86 | 2.45 | 2.16 | Gas |
| 4D | 6,600 | 0.02 | 0.06 | N/A | 13.99 | 2.33 | 0.25 | 0.43 | N/A | 2.06 | Gas |

When predicting maturity or classifying organofacies of a new source rock sample, either in a lab or field setting, similar spectroscopic or optic data can be collected from the new sample of interest, and then analyzed against the data of source rock samples in this database.

Different frequency bands of electromagnetic waves are associated with different molecular responses, which form the physical/chemical basis of various spectroscopic and optic measurement techniques. The UV light response is associated with the energy gap of electronic transitions, and the infrared band produced absorption spectra is characteristic of stretching and bending modes of molecular bonds such as C—H and O—H. The mechanism leading to THz absorption in molecular systems is dominated by excitation of inter as well as intra-molecular vibrations, such as torsional modes in large molecular chains or with intermolecular vibrations between neighboring molecules, which has a more collective character, while the microwave response is typically associated with molecular rotations. Spectroscopic and optic measurements at different wavelengths characterize different aspects of the molecular behavior associated with the structure and compositional change induced by the maturing process and the organofacies variations. Therefore, when optimally combined, data from different types of measurements will provide a more comprehensive characterization that leads to more accurate prediction and classification. These collaborative machine learning and prediction methods help classify the unknown source rock sample.

Figure 5:
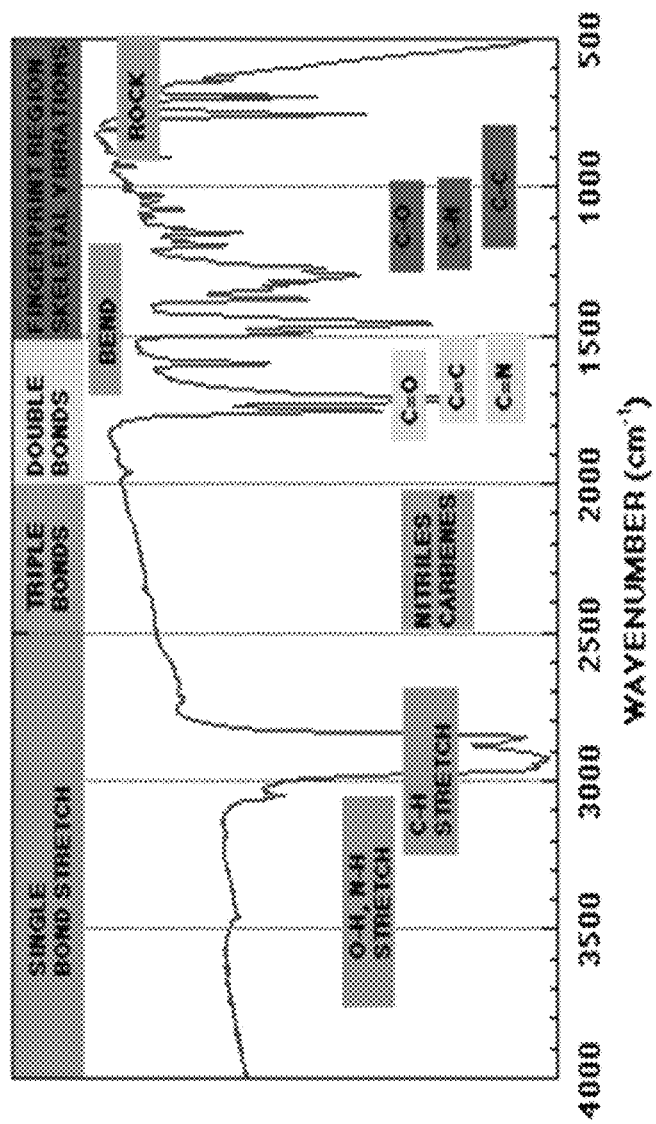
FIG. 5 is an IR absorbance spectrum illustrating the various wave numbers that correspond to chemical functional groups associated with source rocks.

Following are descriptions of certain methods used to characterize various source rock samples in the database. FTIR is a non-destructive analytical method that provides important information for identifying and quantifying mineralogy as well as the composition of the organic matter contained within the rock matrix. In particular, it has the ability to distinguish between aliphatic and aromatic carbon structures associated with the kerogen. This enables the classification of source rocks according to kerogen type and the physical and chemical transformation of the kerogen structure resulting from thermogenic processes. FTIR spectroscopy measures composition and maturity by the use of the vibrational energies corresponding to the structural moieties called functional groups composing the kerogen. These consist mainly of single bond and double bond structures. In particular, changes in the double bonds of C═C and C═O related to the aromatic components and the carbonyl and carboxyl groups, and single bonded C—H related to the methylene (CH2) and methyl (CH3) groups are diagnostic for assessing maturity and composition in kerogen. FIG. 5 is an IR absorbance spectrum illustrating the various wave numbers that correspond to chemical functional groups associated with source rocks. For example, wave numbers of 2930 $cm^{-1}$ and 2860 $cm^{-1}$ are mainly related to the asymmetric and symmetric stretching of the C—H bond of $CH_2$ and $CH_3$. One can use the peak intensities or areas to determine composition relative to the C═O and C═C bond corresponding to wave numbers of 1710 $cm^{-1}$ and 1630 $cm^{-1}$. If the C═O at 1710 $cm^{-1}$ and 1450 $cm^{-1}$ are greater than the $CH_2$—$CH_3$ of C—H bond, then this signals terrestrial organic matter input whereas the opposite relationship suggests more marine input. This relationship indicates that the continuum between these structures can be used to establish whether the organic matter contained is a type I, II, or III kerogen.

Figure 6:
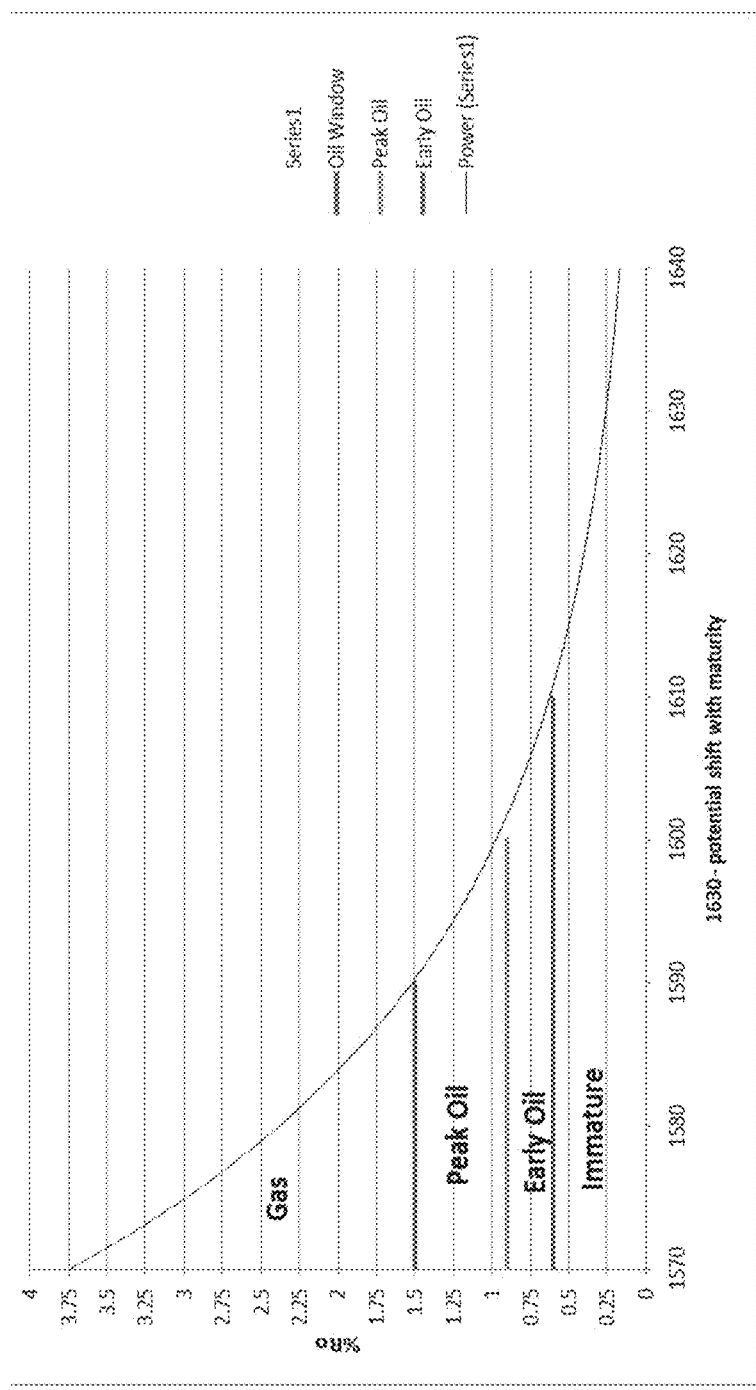
FIG. 6 is a graphical representation depicting the shift to lower wavenumbers with increasing maturity of the source rock samples.

The C═C bond at 1630 $cm^{-1}$ also steadily shifts with increasing maturity due to thermogenic processes. This represents the increased fusion of aromatic rings. One can see this with the relationship between the % Ro and the wave number shift from 1630 to 1570 $cm^{-1}$, as shown in FIG. 6, where there is a shift of the 1630 $cm^{-1}$ wave number with increasing maturity of the kerogens in the source rocks. Moreover, the combination of relationships using the vibrational energies 2930 $cm^{-1}$ and 2860 $cm^{-1}$ and 1630 $cm^{-1}$ can be used to develop a Van Krevelen diagram. In addition to the composition and classification of organic matter, the FTIR can be used to identify and quantify mineral compositions. With the ability to identify mineralogy of the source rocks, one can then use this information along with that of the kerogen composition derived from FTIR to define an organofacies profile. Organofacies reflects the complexity of the source rock related to the depositional environment, maceral type and tectonic province.

THz spectroscopy is another nondestructive analytical method to analyze source rock. THz radiation are electromagnetic waves in the frequency range of 0.3-10 THz (1 THz=1012 Hz), located in the spectrum between microwaves and the near infrared. THz absorption is dominated by the excitation of long-range vibrations, either intramolecular torsional modes in large chains or intermolecular vibration modes between neighboring molecules. These low-frequency vibrational modes are highly collective and may mix considerably. As a result, association of individual absorption bands or peaks with specific modes and molecular structure and composition is generally known to be a difficult task. As a result, interpretation of THz spectroscopy data in the context of source rock characterization has been scarce in the literature. In certain embodiments, the methods of analyzing the source rock samples include juxtaposition of THz data with FTIR data for samples of the same level of maturity and organofacies types, in such a way that the association of THz data with molecular properties are inferred from those of FTIR data, which have been better characterized. The resulting THz association is stored in the database and is used to predicting properties of new samples with their own THz data.

ESR spectroscopy in the electron spin resonance range provides measurements of characteristics such as color intensity, spin number, and aromatic carbon population per spin. The intensely dark color of the resin and asphaltene fractions of petroleum is believed to be indicative of organic free radicals usually associated with aromatic structure.

Fluorescence microscopy (FM) is an optical tool used for the identification, classification and quantification of both organic and inorganic materials. Fluorescence is a luminescence property, where photons are used to excite susceptible electrons within the atomic structure of minerals, organic matter, and geologic materials. These excited electrons temporarily jump up to a higher orbital within the mineral's atomic structure. When those electrons fall to their original orbital, energy is released in the form of light. The emitted fluorescent light has a longer wavelength and lower energy than the excitation light (Stoke's shift). Source rocks with different thermal maturities, related to hydrocarbon chain length, have characteristic Stoke's shifts. According to the Einstein-Planck equation, lowering absorption energy results in longer emission wavelength, the well-known fluorescence red-shift accompanying thermal maturation of organic matter. Decreasing fluorescence emission intensity at higher maturity is due to the concentration quenching effect (non-radiative relaxation) of increased molecular aromatization, which decreases fluorophore density. Some of the organic matter present in source rock is a biopolymer which comprises primarily of long-chain saturated aliphatic hydrocarbons. The diagnostic potential of fluorescence images combined with spectral data provides an opportunity for rapid source rock and organofacies analysis.

Gas chromatography (GC) and gas chromatography-mass spectrometry (GC-MS) data are collected to analyze for hydrocarbon molecular chemistry associated with oil or bitumen extracted from the source rock. In certain embodiments, the source rock sample is subject to five main steps of organic geochemical analysis. In the first step, the source rock is subject to Rock-Eval® pyrolysis, followed by a second step of one of several methods of solvent extraction, such as Soxhlet, ultrasonic, liquid-liquid extraction, to extract bitumen. In the third step, the bitumen is subject to high-performance liquid chromatography to analyze saturates, aromatics, NSO compounds, and asphaltenes. The saturates and aromatics are further analyzed in a fourth step using gas chromatography to understand the n-alkanes ($C_{22}$-$C_{35}$) and aromatics ($C_{22}$-$C_{35}$) profile. These compounds are further analyzed by GC-MS to obtain a biomarker profile. The data is useful for a large number of assessments, such as assessment of the pristane and phytane molecules to determine depositional environment, oil to oil correlations using isoheptane invariance to determine whether produced fluids originated from the same source rock within a basin, and even-odd alkane carbon number ratio to determine organic matter type. API gravity (American Petroleum Institute gravity) is calculated using the specific gravity of an oil, which is the ratio of its density to that of water (density of the oil/density of water). Specific gravity for API calculations is always determined at 60 degrees Fahrenheit (° F.). The GC-MS data can be used to detect changes in API gravity due to evaporative fractionation or biodegradation of oils. The GC-MS data can also be used to detect and assess oil properties and degree of biodegradation. The methods disclosed here use molecular chemistry of produced fluids to develop a method for predicting API gravity across a basin for source rock reservoirs and conventional reservoirs. Gas-chromatography/mass spectrometry data can also be used to analyze oils and extracted bitumen for biomarkers from both saturate and aromatic fractions. The GC-MS data can be used to detect the isomerization and aromatization of certain biomarkers to estimate maturity of the fluids in source rocks and establish whether hydrocarbons were generated in situ or migrated from another location. The GC-MS data can also be used for establishment of organofacies using depositional biomarkers. The GC-MS data can be used in Diamondoid analysis to determine the percentage of oil to gas cracking in the source rock and its relationship to development of intra-kerogen porosity, and to determine whether the oil is originating from the same or different source rocks and or reservoirs. The GC-MS data can be used in time series geochemistry of biomarkers in produced fluids as compared to biomarkers extracted from bitumen to determine where production originates within the stimulated rock volume. Once the database of multiple measurements from representative samples is established, and measurements of new samples of interest are obtained, one or more of the analysis methods for prediction of maturity and organofacies profile can be undertaken. A method includes data preprocessing, extraction of features, determination of optimal maturity and organofacies attributes for lab setting and field setting, classification of source rock sample and prediction and interpretation of maturity/organofacies profile.

The disclosure also provides for a system to determine maturity of a sample source rock. The system includes a plurality of data acquisition devices placed in vicinity of a sample source rock and communicatively coupled to one or more processors. The system also includes a non-transitory, computer-readable medium positioned in communication with the one or more processors and having a computer program stored thereon including a set of instructions that when executed by one or more processors causes the one or more processors to perform operations of: establishing a communication link with a plurality of data acquisition devices placed in vicinity of a sample source rock, obtaining a first plurality of data of a sample source rock from the plurality of data acquisition devices, and analyzing the first plurality of data using a predictive correlation to determine maturity of the sample source rock. The predictive correlation is generated by the data analysis engine by applying a machine learning model to correlate a second plurality of data acquired from a plurality of representative source rocks with a plurality of properties of the plurality of representative source rocks. The system also includes the source rock database containing at least the second plurality of data associated with the plurality of representative source rocks, the plurality of properties of the plurality of representative source rocks, and the predictive correlation. The data acquisition devices can be positioned to acquire data from optimal sensing bands of the sample source rock. The data acquisition devices are positioned to acquire two or more of location data, spectral measurements, and optical measurements. The system can include a sample source rock retrieving apparatus to obtain a portion of the sample source rock. The spectral measurements can include one or more of measurements obtained from Fourier Transform Infrared spectroscopy, Electron Spin Resonance spectroscopy, THz spectroscopy, and Ultraviolet spectroscopy. The optical measurements can include one or more of measurements obtained by fluorescence microscopy and confocal laser scanning microscopy. For example, in certain embodiments, images from confocal laser scanning microscopy analysis have a pixel size of 400 nanometers (nm) when the instrumentation has a resolution of 200 nm.

Also, disclosed here are specialized sampling devices. These devices include a sampling inlet and a sample acquisition chamber. The sampling inlet is designed to extract samples from the drilling environment. Samples can include fluids, solids, or combinations thereof. In certain embodiments, the sample is a source rock sample that is not a component of the drilling fluid stream. The sample acquisition chamber can be equipped to store the sample without loss of integrity until further processing. The sample acquisition chamber can be equipped to place the sample in contact with in situ data acquisition devices for further processing. The sampling inlet can be designed to contain one or more openings to allow passage of sample retrieval devices, samples, or both. Sample retrieval devices include both sample extraction components and sample collection components. Sample extraction components can include mechanical manipulators such as a drill, or devices that use fluids, such as water or air, or waves such as ultrasonic waves to extract samples. Source rock samples can be extracted using mechanical manipulators or fluid-based drilling instruments. Sample collection components can be integrated into the sample extraction component or can exist separately, such as a container or a suction device that collects the sample after it is separated from the environment.

An example of a data acquisition device is a downhole spectrometer, and includes a at least a light source, a detector, a component to reflect light from the source of the material of interest (whether fluid or rock) and back at the detector, components to deploy the source and detector into a well, and components to retrieve data obtained in the spectral measurement. In one embodiment, the light source is one or more single chip lasers (such as indium gallium antimonide distributed feedback lasers or a quantum cascade laser), each tuned to produce a different wavelength and each powered separately so that only one such laser is activated at a time. In this embodiment, the detector is a pyroelectric detector made of, for example, lanthanum titanate ($LaTiO_3$). Pyroelectric detectors do not generate carriers by absorption. Rather, they generate a charge by electromechanical expansion due to heating from the incident photons. Thus, they are sensitive to a broad range of frequencies, and one such pyroelectric detector could be used to measure light intensity from any of the single chip lasers. In this embodiment, the lasers are activated one at a time, and the light intensity detected by the pyroelectric detector is measured and recorded in a computer memory when each laser is active, providing a measure of the attenuation of light at each laser wavelength.

In an embodiment, the light source can be an iron wire which, upon heating, radiates a broad spectrum of light in the infrared band. In this embodiment, the detector is multiple pyroelectric detectors, where each detector has a permanent optical filter on top of it, so that it is only sensitive to light at the wavelength selected by the filter. When the light source is active, the intensity of light at each pyroelectric detector is recorded providing a measure of the attenuation of light at the wavelength selected by each of the filters. In one embodiment, there are multiple pyroelectric detectors with filters tuned to each wavelength. Each such detector is much smaller than the width of the light beam, and all detectors are placed in a checkerboard pattern within the light beam of the source. The light intensity at all the detectors with filters of the same wavelength is summed such that variations in the light beam intensity are averaged over the many detector locations. In an embodiment, the means to reflect light off the material includes a chamber into which a rock or fluid sample is introduced. The source and detector are outside the chamber, and light passes from the source, through a window into the chamber, and then back though the same window to the outside of the chamber where it is measured by the detector. In another embodiment, the source and detector are contained in a sensor package, separated from wellbore fluids or rock face by a window. In an embodiment, the window is coated on the rock sample or fluid side with a nonstick coating such as parylene, which repels wellbore fluids so that said fluids are visible through the window but do not stick to the window. In an embodiment, the window is disposed in proximity to a mechanical claw or scraper which removes drilling mud from the rock face, such that light can pass from the source to the rock face and reflected light from the rock face can be observed by the detector. In another embodiment, a jet of transparent fluid is sprayed on the rock face to maintain a transparent fluid layer between the window and the rock face.

In certain embodiments of a data acquisition device, the light source and detector are deployed into the well as contained within a wireline tool, or a drill string, or a slick line tool, or a drilling sub, or a bottom hole assembly, or in combinations thereof. In certain embodiments, the raw spectrometric data are (a) stored in computer memory in the tool for downloading after the tool is recovered from the well, or (b) transmitted to the surface along a cable, or (c) telemetered to the surface using a means of wireless telemetry including acoustic telemetry, electromagnetic telemetry, or mud pulse telemetry.

Different aspects of the reservoir analysis can be incorporated into the data acquisition devices. Certain embodiments have tunable optical elements that can measure directly in situ compositions of minerals and bitumen components, and provide information about hydrocarbon reserves in shales and carbonates.

Certain embodiments include apparatuses and methods for acquiring downhole infrared spectroscopy measurements. Infrared spectroscopy provides information about the organic and mineral content of rocks, as well as information to distinguish and characterize the produced fluids. However, such measurements are currently made in the lab on recovered samples, because the instruments required are bulky and the standard spectroscopy instrument designs require detectors that cannot operate at downhole temperatures. The apparatus described here acquires the spectroscopy measurements using small, robust components, which can operate at downhole temperatures. In an embodiment, the device includes a broad-spectrum infrared source and pyroelectric detectors with specific fixed integrated optical filters in an attenuated reflectance spectroscopy scheme. In another embodiment, the device includes using laser chips at selected frequencies and either pyroelectric or quartz enhanced photoacoustic spectroscopy detectors. With a multitude of such small, single wavelength attenuation measurements, spectral information at key wavelengths can be obtained rapidly, at all depths in the well, and at a fraction of the cost of laboratory measurements, even at downhole temperatures. These infrared absorption logs have several applications. The infrared absorption of the rock face in the wellbore at key wavelengths is related to mineralogy and maturity to guide drilling and hydraulic fracturing of shale gas wells. Such logs in the vertical part of the well would indicate the optimal depth for the laterals, and such logs in the laterals would indicate the optimal locations for hydraulic fracturing. Such logs would also enable basin models and geological understanding of the hydrocarbon system to be refined and updated as new wells are drilled. Infrared absorption logs of the fluid within a producing well provide information about the composition of the fluid, which can indicate the origin of the fluid and thus the compartmentalization of the reservoir.

Example 1

The source rock database contains measurement of various characteristics of source rock samples. For example, without limitations, the source rock database contains parameters associated with various source rock samples, such as location and depth, and their Rock-Eval® parameters, such as S1, S2, Tmax, HI, oxygen index (OI), production index (PI), TOC, % Ro-Tmax, and HI-% Ro. The source rock database can also contain FTIR data, such as the raw and pre-processed data, FTIR imaging data, and FTIR data of extracted samples, and elemental composition data including individual mineral maps and mineral distribution of the source rock samples. The source rock database also contains spectral measurement and images, confocal fluorescence images, X-ray fluorescence images, ESR measurements, THz images, and other data. Provided below are the various methodologies used to obtain these measurements and examples of data included in the database.

The FTIR spectra of all the representative source rock samples were obtained over wavenumber band 500-4000 $cm^{-1}$. The measurements were taken from the same source rock samples as in Table 2 in powder form with varying particle sizes, including extracted kerogen as well as clay fractions. Kaolinite, illite, montmorillonite, and Na-montmorillonite clay samples with varying particle sizes ranging from 45 to 250 microns were used, such as montmorillonite-45, montmorillonite-63, montmorillonite-75, kaolinite-106, kaolinite-150, illite-150, illite-150, montmorillonite-150, and 250 microns. The extracted kerogen is approximately 100% by volume and clay is also 100% in trace by selective etching. Analyzed in powder form, the clay fractions appear less dependent on the source rock maturity as the extracted kerogen.

Figures 7A, 7B, 7C:
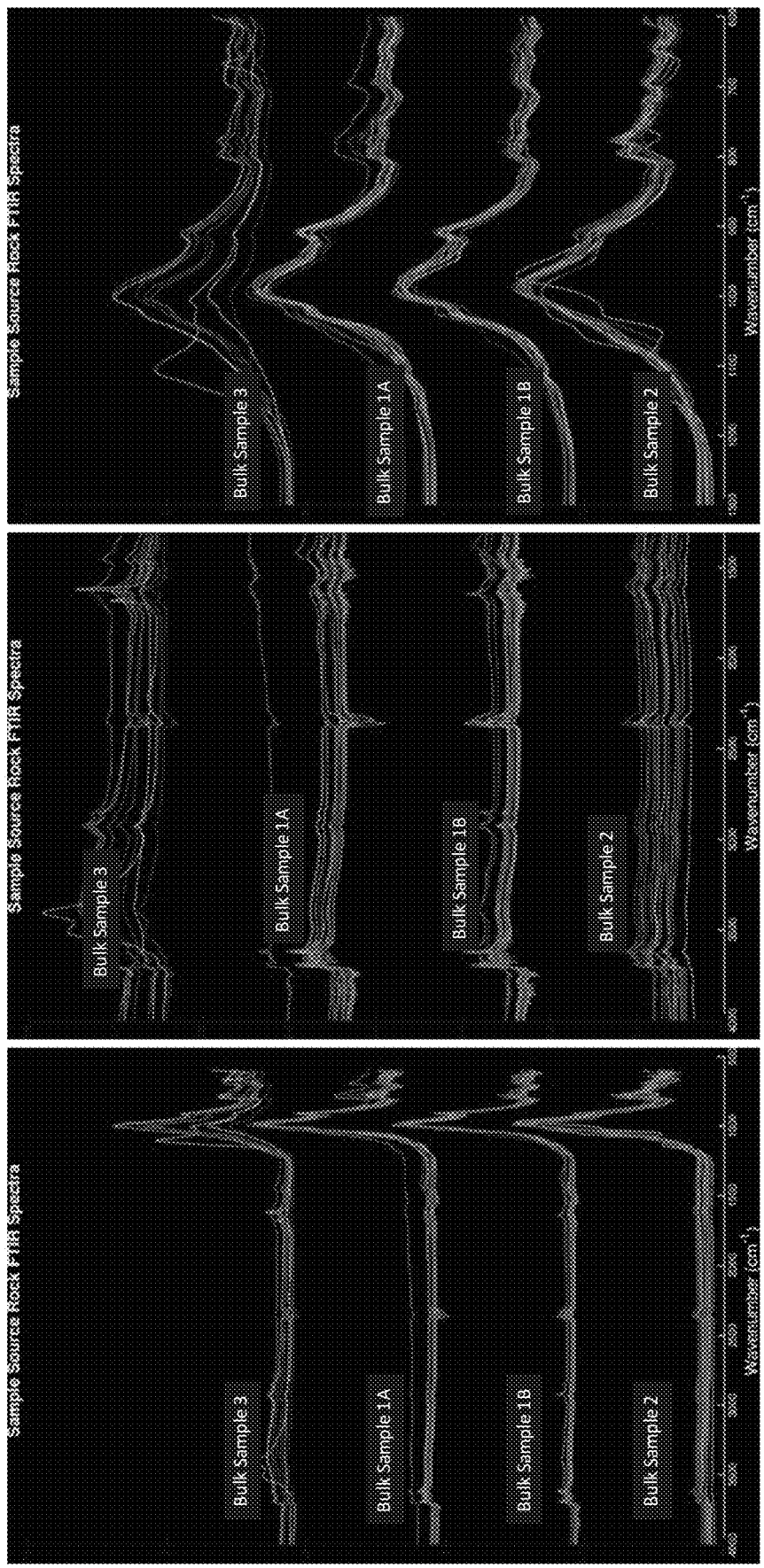
FIG. 7A is the FTIR spectroscopy spectra for four groups of source rocks, separated according to respective maturity, increasing from top to bottom.
FIG. 7B is a magnified view of FTIR spectra for the four groups of bulk source rocks analyzed in FIG. 7A.
FIG. 7C is a further magnified view of FTIR spectra for the four groups of bulk source rocks analyzed in FIG. 7A.

FIG. 7A is the FTIR spectra for four groups of source rocks, separated according to respective maturity, increasing from top to bottom. FIG. 7B is the magnified view of FTIR spectra for the four groups of bulk source rocks analyzed in FIG. 7A, for better visualization of the bands associated with organic content. Wave numbers of 2930 cm$^{-1}$ and 2860 cm$^{-1}$ are mainly related to the asymmetric and symmetric stretching of the C—H bond of $CH_2$ and $CH_3$. In FIG. 7B, it is evident that the peaks at 2930 cm$^{-1}$ and 2860 cm$^{-1}$ decreases from Samples 3, 1A, 1B to Sample 2, as the maturity increases (Table 2). One can also use the peak intensities or areas to determine composition relative to the C=O and C=C bond corresponding to wave numbers of 1710 cm$^{-1}$ and 1630 cm$^{-1}$ (FIG. 7B). FIG. 5 shows an FTIR spectra in terms of Transmittance (T). Most of the other FTIR spectra provided in this disclosure, including FIGS. 7A, 7B, and 7C and beyond, use the Absorbance (A) representation. Note that A=log 10(1/T) which explains the inversion of the peaks compared to those in FIG. 5. FIG. 7C is the magnified view of FTIR spectra for the four groups of bulk source rocks analyzed in FIG. 7A, for better visualization of the bands associated with clays and mineral content. Unlike the bands mentioned in FIG. 7B, the variations in the clay and mineral bands do not have well known direct dependence on maturity, at least not visually evident from the FTIR spectra. One of the purposes of methods disclosed here is to infer and capture these relationships by correlating these variations across different bands over the same set of samples. Wave numbers of 2930 cm$^{-1}$ and 2860 cm$^{-1}$ are mainly related to the asymmetric and symmetric stretching of the C—H bond of $CH_2$ and $CH_3$. In FIG. 7B, it is evident that the peaks at 2930 cm$^{-1}$ and 2860 cm$^{-1}$ decreases top down from Bulk Sample 3, Bulk Samples 1A and 1B to Bulk Sample 2, as the maturity increases. One can also use the peak intensities or areas to determine composition relative to the C=O and C=C bond corresponding to wave numbers of 1710 cm$^{-1}$ and 1630 cm$^{-1}$.

Figures 8A, 8B:
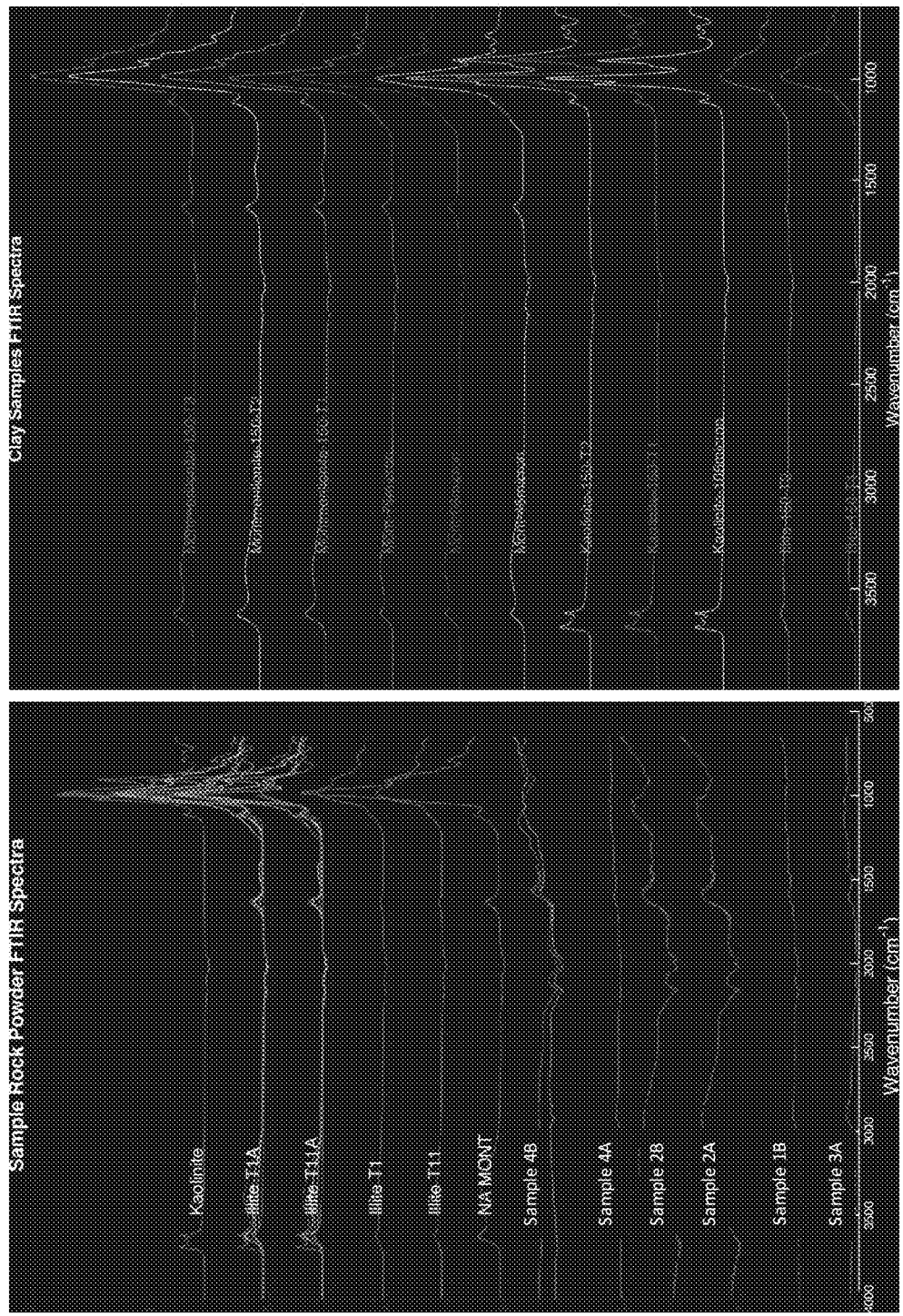
FIG. 8A is the FTIR spectra for several source rock powder samples as well as extracted kerogen.
FIG. 8B is the FTIR spectra for pure clay powder samples.

FIG. 8A is the FTIR spectra for several source rock powder samples as well as extracted kerogen, versus FIGS. 7A and 7B as ATR FTIR measurements from bulk samples. The FTIR spectra of the extracted kerogen from Samples 1B, 2A, 2B, 3A, 4A and 4B have significantly lower response in the clay and mineral bands compared to those of clay powders, as expected. In addition, the peaks near the C—O and C—C bands are more pronounced. The spectra shown in FIGS. 7 A, 7B, and 7C are attenuated total reflectance (ATR) FTIR measurements taken from bulk source rock samples, while those in FIGS. 8A and 8B are measurements from powder samples of source rocks and reference clay samples.

FIG. 8B is a plot of the FTIR spectra for pure clay powder samples, where the clay samples show very little response at the C—H bands. Instead, the characteristic signals near 3600 cm$^{-1}$ are evident, especially for the kaolinites, the bunny ear like peaks stand out. All the clay samples also show strong peaks around 1000 cm$^{-1}$ associated with mineral responses. Kaolinite, illite, montmorillonite, and Na-montmorillonite clay samples with varying particle sizes ranging from 45 to 250 microns were used, such as montmorillonite-45, montmorillonite-63, montmorillonite-75, kaolinite-106, kaolinite-150, illite-150, illite-150, montmorillonite-150, and 250 microns.

Figures 9A, 9B:
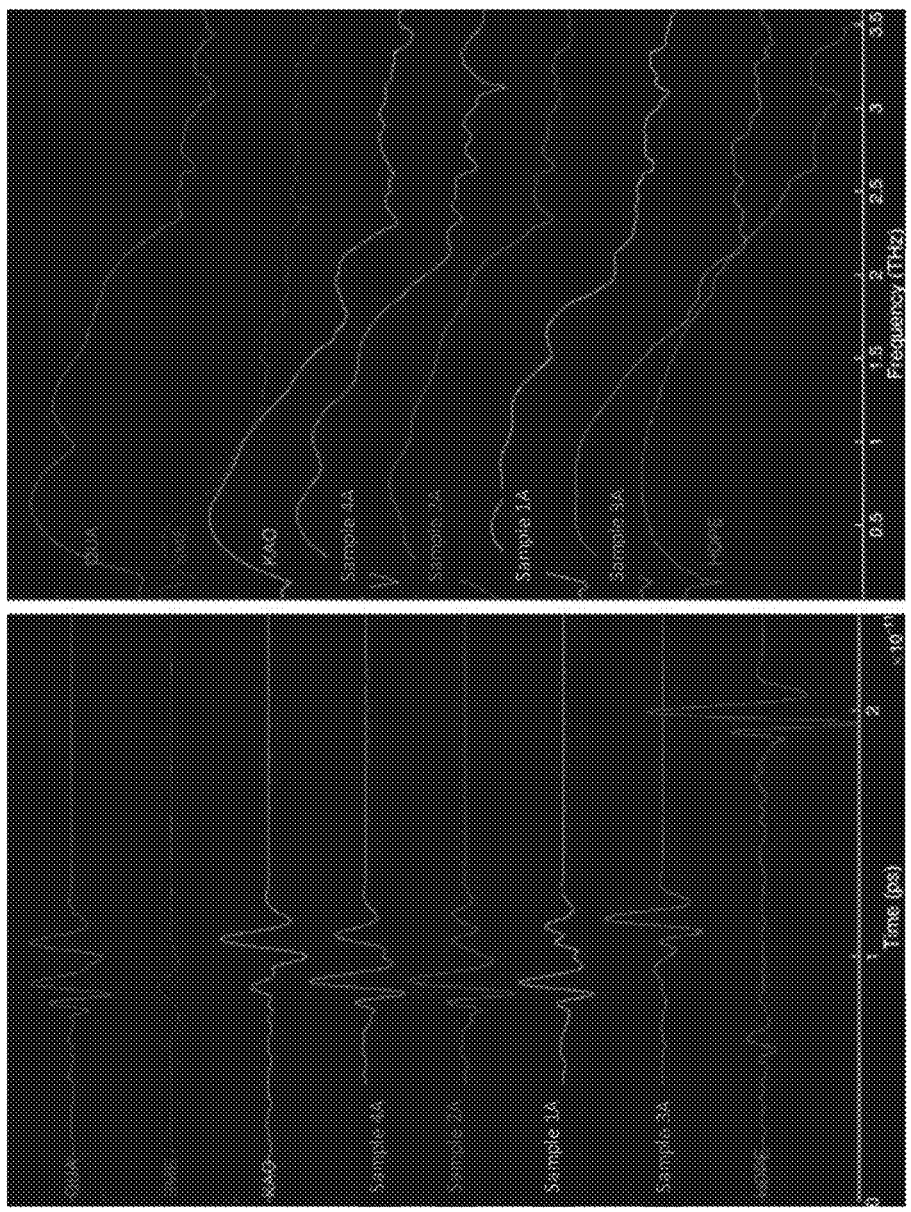
FIG. 9A depicts the measured time trace of a terahertz reference (high-density polyethylene (HDPE)) and the pulse time waveforms from the analysis of the various source rock samples.
FIG. 9B is the corresponding spectra obtained by Fourier transformation of the waveforms.
Figures 10A, 10B:
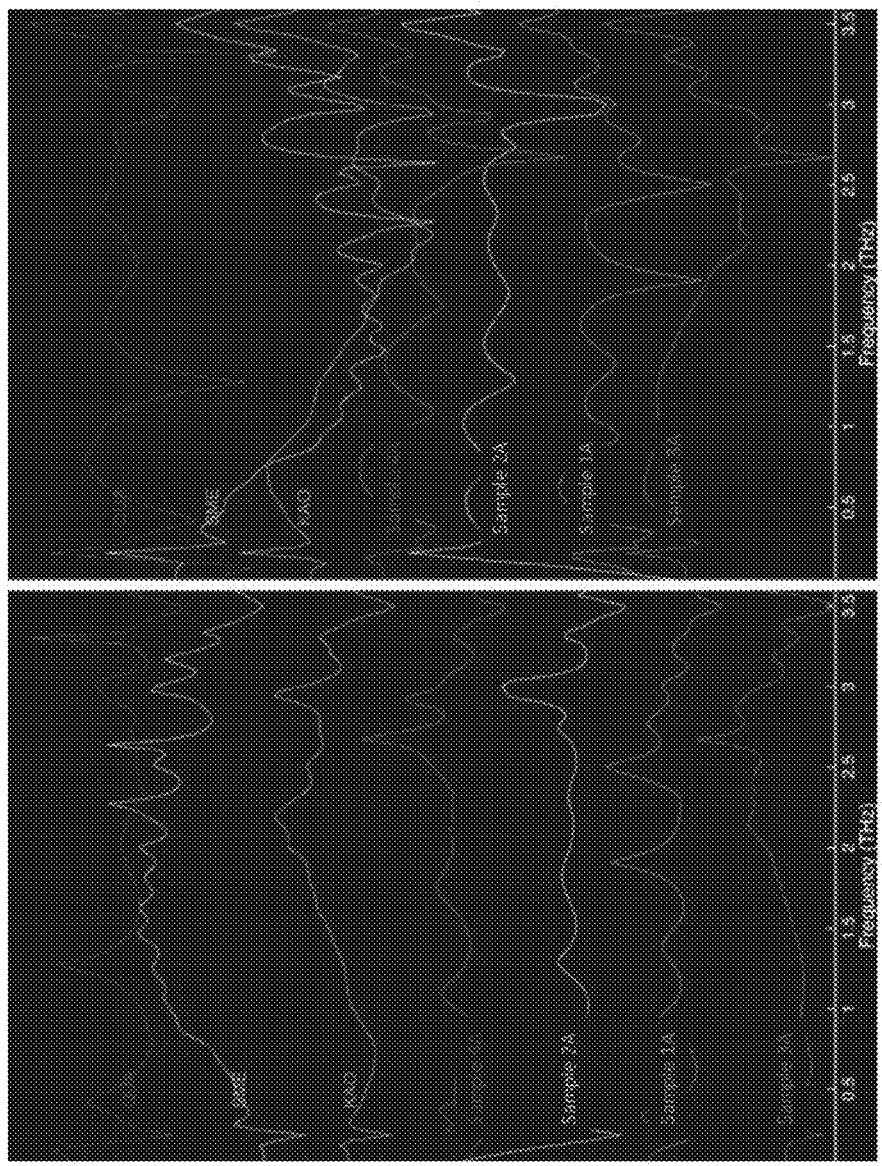
FIGS. 10A and 10B depict the sample absorbance and transmittance spectra of the various source rock samples analyzed in FIGS. 9A and 9B, in terahertz band.

The THz spectroscopy data in the source rock database is obtained using the THz time-domain spectroscopy (THz-TDS) methodology. FIGS. 9A, 9B, 10A, and 10B are the THz time-domain spectroscopy data of source rock samples. FIG. 9A shows the measured time trace of a THz reference (HDPE) and the pulse time waveforms from the analysis of the various source rock samples, and FIG. 9B is the corresponding spectra obtained by Fourier transformation of the waveforms. Based on that, the sample absorbance and transmittance spectra of the various source rock samples were computed and shown as the THz absorbance spectra in FIG. 10A and transmittance spectra in FIG. 10B of source rock samples. As shown in FIGS. 10A and 10B, the association of THz spectral band to organic molecular structures is not as straightforward and less well defined. It is believed that most of the signatures can be related to intramolecular torsional modes in large chains or intermolecular vibration modes between neighboring molecules. By collaboratively learning methods disclosed here, the THz data is juxtaposed with other measurements such as FTIR spectra for samples of the same level of maturity and organofacies profile. The resulting THz association is a trained model that can be used to identify the characteristic structures of new rock samples, such as their organic content, by their representative THz data.

Figure 11A:
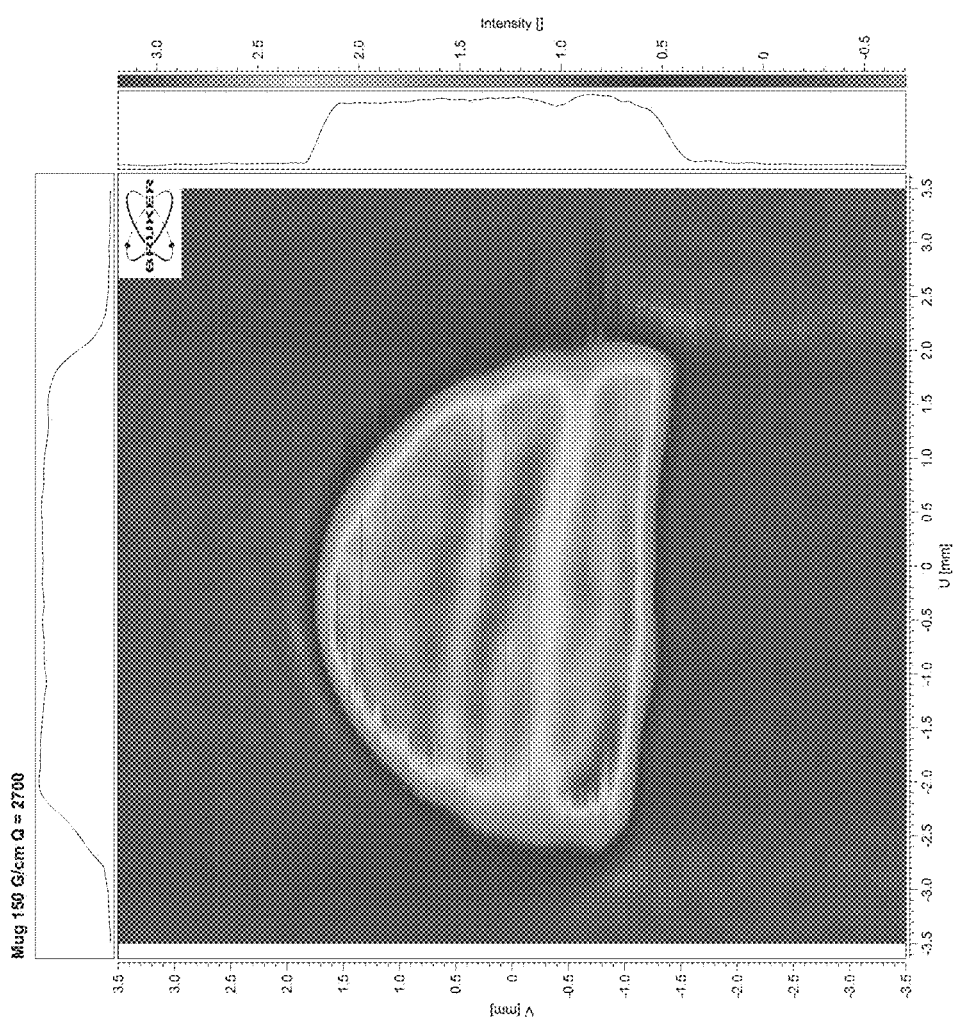
FIG. 11A is a two-dimensional (2D) core cross section showing bedding of a source rock (red area is rich in organics).
Figure 11B:
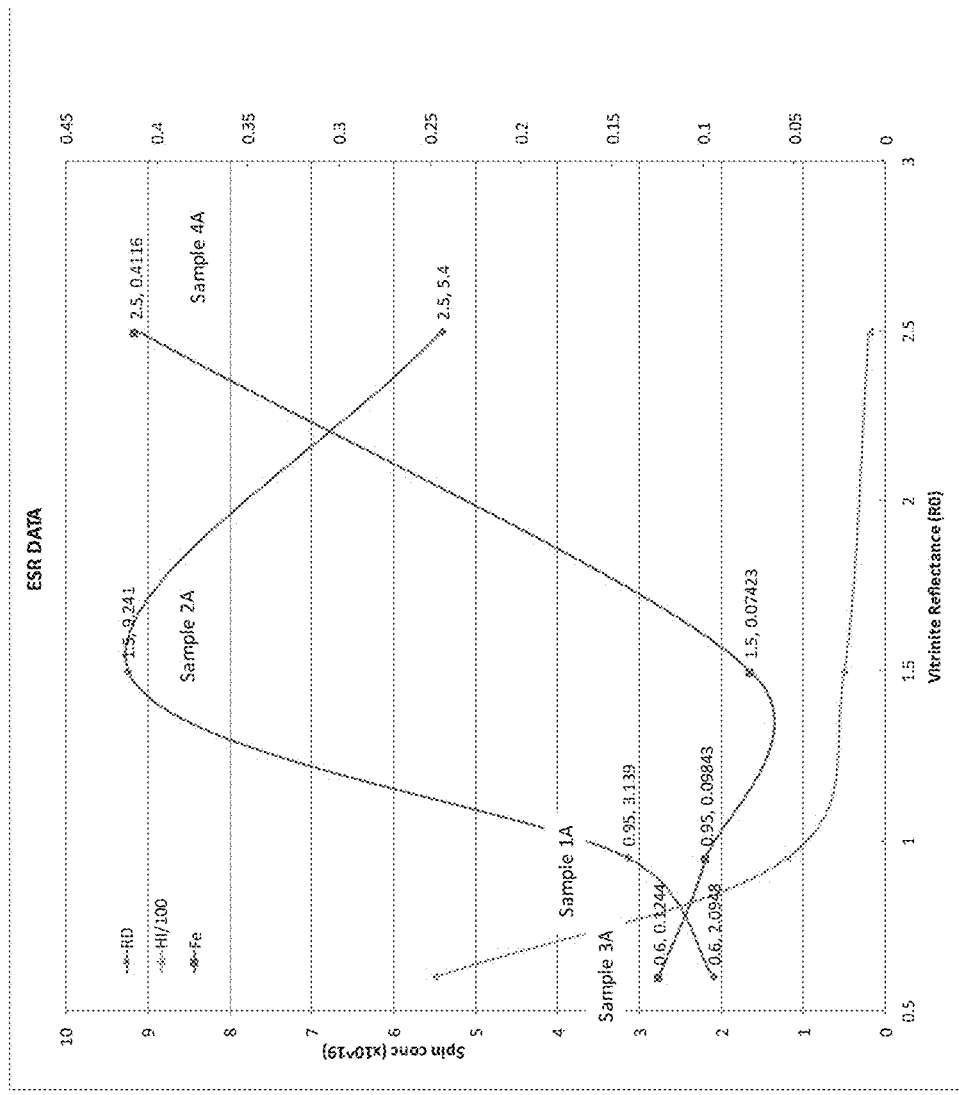
FIG. 11B is a graphical representation of the vitrinite reflectance plotted against the hydrocarbon index for source rocks of four different maturity levels, identified as Sample 1A, Sample 2A, Sample 3A, and Sample 4A.

ESR spectroscopy was used to analyze source rocks of four different maturity levels. FIG. 11A is a 2D core cross section showing bedding in transmission (red area is rich in organics). The color scale represents the levels of free radicals as they vary across the sample with red being higher level. FIG. 11B is a graphical representation of the free radicals, the iron and the hydrocarbon index as a function of vitrinite reflectance for source rocks of four different maturity levels—Samples 4A, 2A, 1A and 3A, as described in Table 2. The free radical and pyrite responses are obtained in a bulk measurement. There is a parabolic dependence of the pyrite/free radical concentration with increasing maturity. In the ESR image, the source rock sample is Sample 3A, showing organic richness (orange colored), and the plot in FIG. 11B shows the spatially averaged compositional difference, in terms of free radicals (RD curve in blue), pyrite (Fe curve in red) and Hydrogen Index (HI/100 in green).

Figures 12A, 12B, 12C:
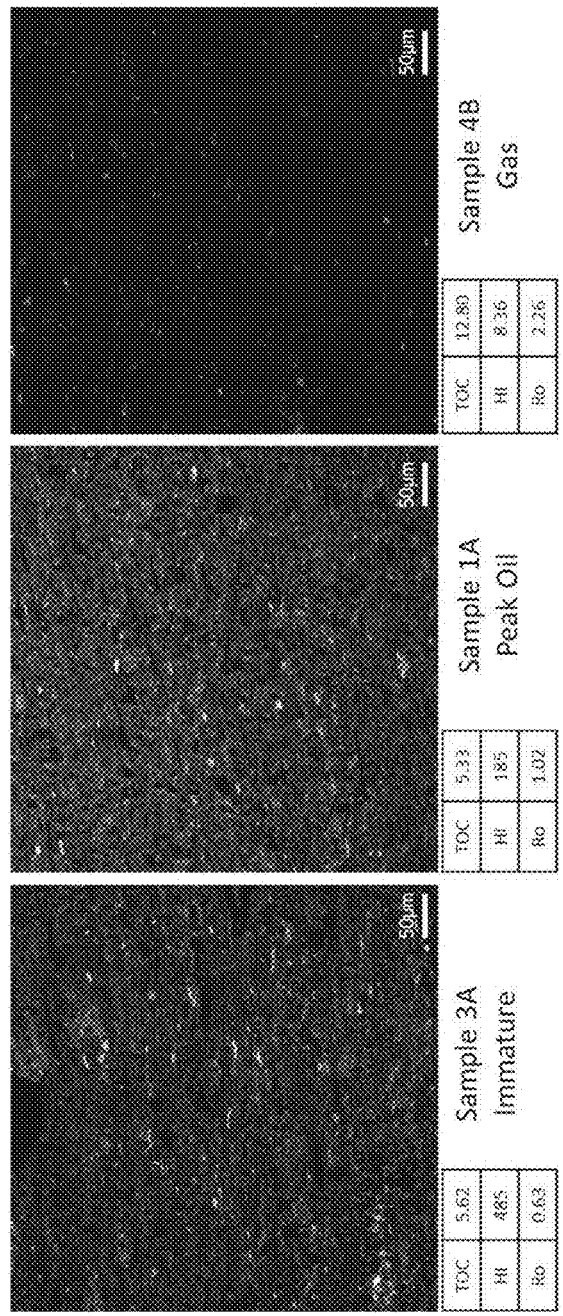
FIGS. 12A-12C provide examples of fluorescence measurements on source rock and oils.

FIGS. 12A-12C illustrate the relative fluorescence response of organic rich source rock samples of varying maturity. Fluoresce intensity of organic matter decreases as with maturity. The confocal images were taken on cleaned, cut, and ion milled samples. The samples had smooth. These images were acquired with a laser scanning confocal microscope. The samples were excited with a series of three lasers (405 nm, 488 nm, and 633 nm). The emission range for the 405 nm excitation was 400-513 nm. For the 488 nm laser the emission range was 490-633 nm. Finally, for the 633 nm laser the emission range was 638-747 nm. The images correspond to fluorescence intensity of light emitted. The colors represent emitted light detected through a series of filters at approximately 490 nm, 505 nm and 560 nm. As shown in FIG. 12A, Sample 3A is an immature sample with a hydrogen index (HI) of 485. There is a strong florescence response in Sample 3A relative to the more mature samples. As shown in FIG. 12B, Sample 1A is in the peak oil window, with an HI of 185. As shown in FIG. 12C, Sample 4B is well within the gas window with an HI of ~8. There is an increase in maturity (loss of hydrogen and therefore lower HI) corresponding to a decrease in the fluorescence intensity. Although these examples show qualitative decreases, this response can also be captured quantitatively.

Using the source rock database of multiple measurements from representative samples, and measurements of new samples of interest, the analysis process for maturity and organofacies prediction consists of several steps, including preprocessing, feature extraction, optimal maturity and organofacies attributes for lab setting and field setting, source rock classification and maturity/organofacies prediction and interpretation. In certain embodiments, samples can be retrieved and processed before further presentment for analysis. For example, samples can be presented as thin sections. Samples can also be presented as large fragments that are mounted and smoothed by mechanical polishing or by ion milling. Samples can also be presented as small fragments of the core that are mounted and smoothed by mechanical polishing or by ion milling. Certain analytical methods may require sample cleaning as part of sample preparation, as the presence of external compounds such as drilling muds can influence the analysis.

Figure 13:
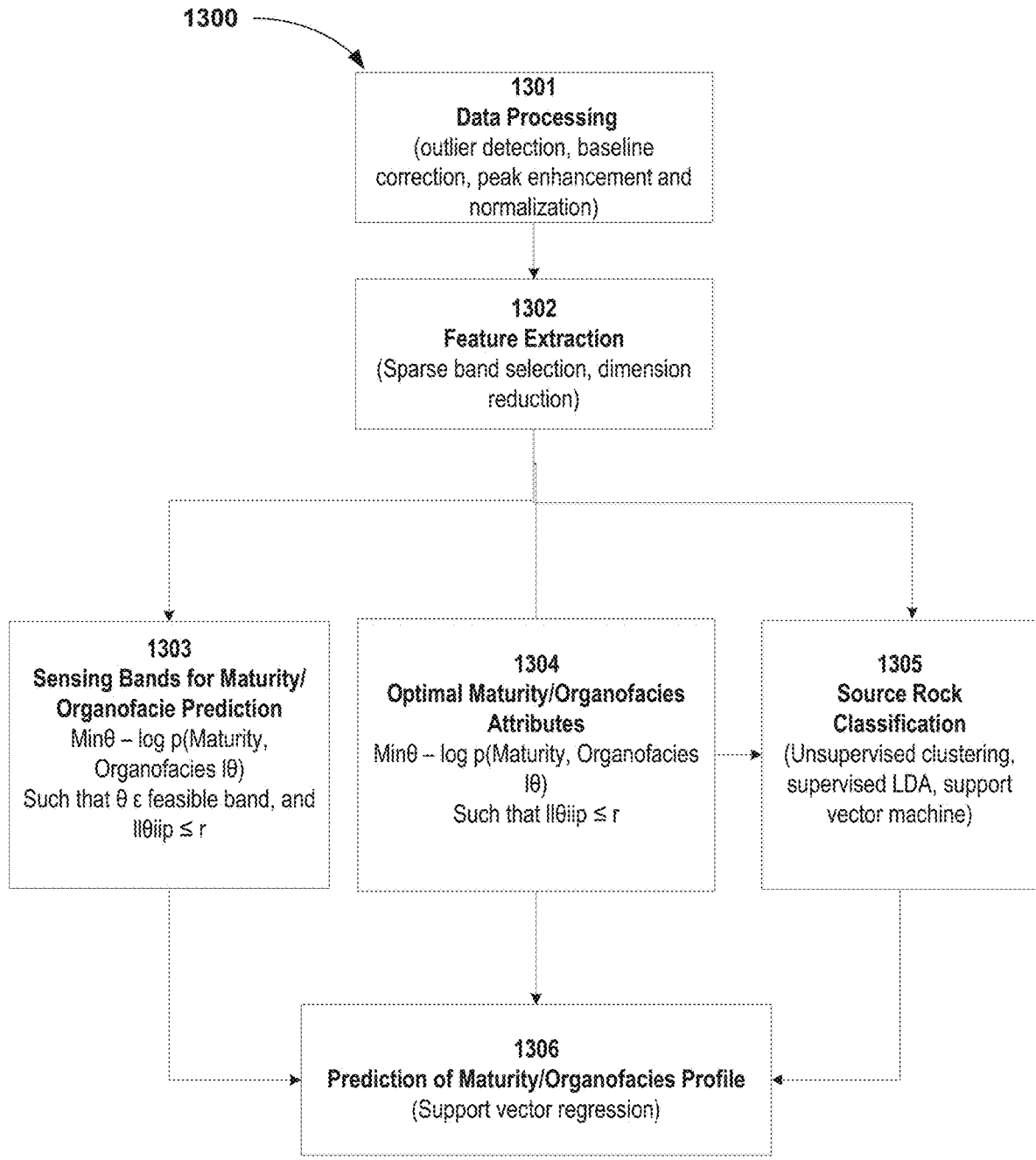
FIG. 13 is a flowchart illustrating a method to predict the maturity and organofacies profile of a sample source rock, according to an embodiment.
Figures 14A, 14B:
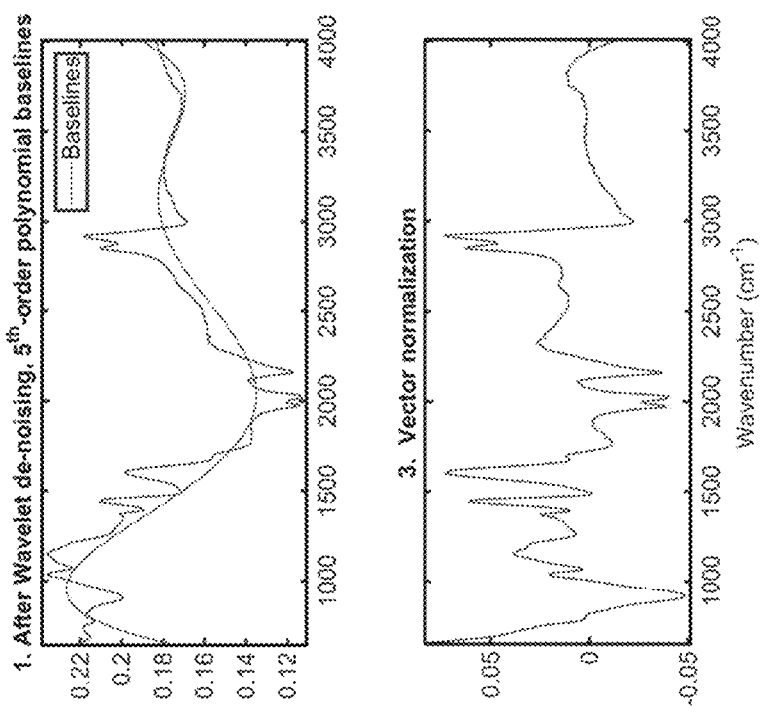
FIGS. 14A-14D are representations of pre-processing of FTIR data from a source rock, Sample 3A.
Figures 14C, 14D:
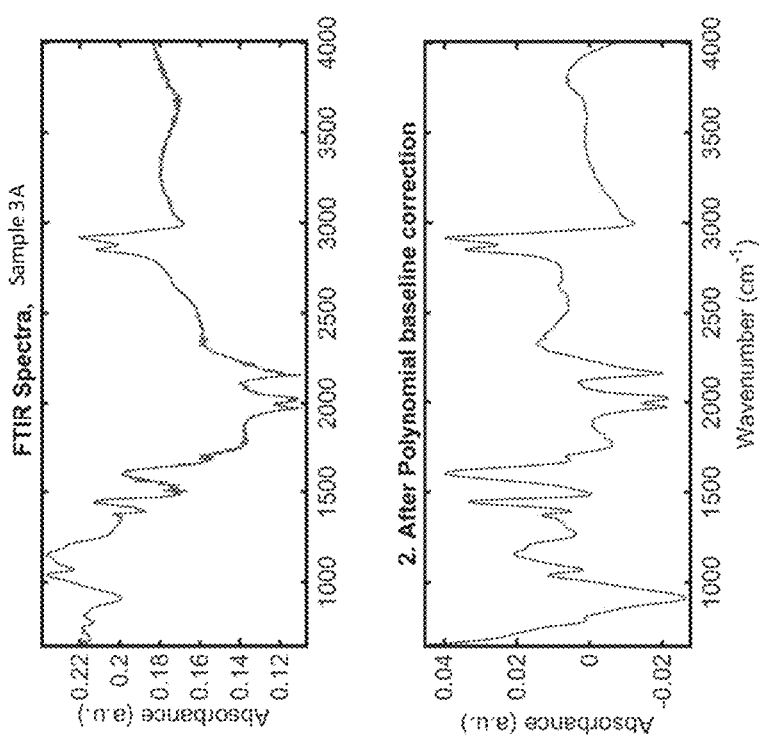

FIG. 13 is a block diagram of a method 1300 to predict the maturity and organofacies profile of a sample source rock, according to an embodiment. The method begins with the processing of the data acquired from the source rock samples by methods previously described. The data processing step 1301 includes data cleaning and preparation steps for each type of measurement, such as outlier detection, baseline correction, peak enhancement and normalization. Outlier detection can be achieved via many techniques such as principal component analysis or proximity-based approaches. An example of FTIR data from source rock sample, Sample 3A, is subject to these processing steps, as shown in FIGS. 14A-14D. FIG. 14A is the raw FTIR data from source rock sample, Sample 3A. FIG. 14B shows the FTIR data subject to wavelet de-noising and baseline correction. FIG. 14C shows the FTIR data after $5^{th}$ order polynomial baseline correction. FIG. 14D shows the FTIR data of FIG. 14C subject to vector normalization.

Figure 15:
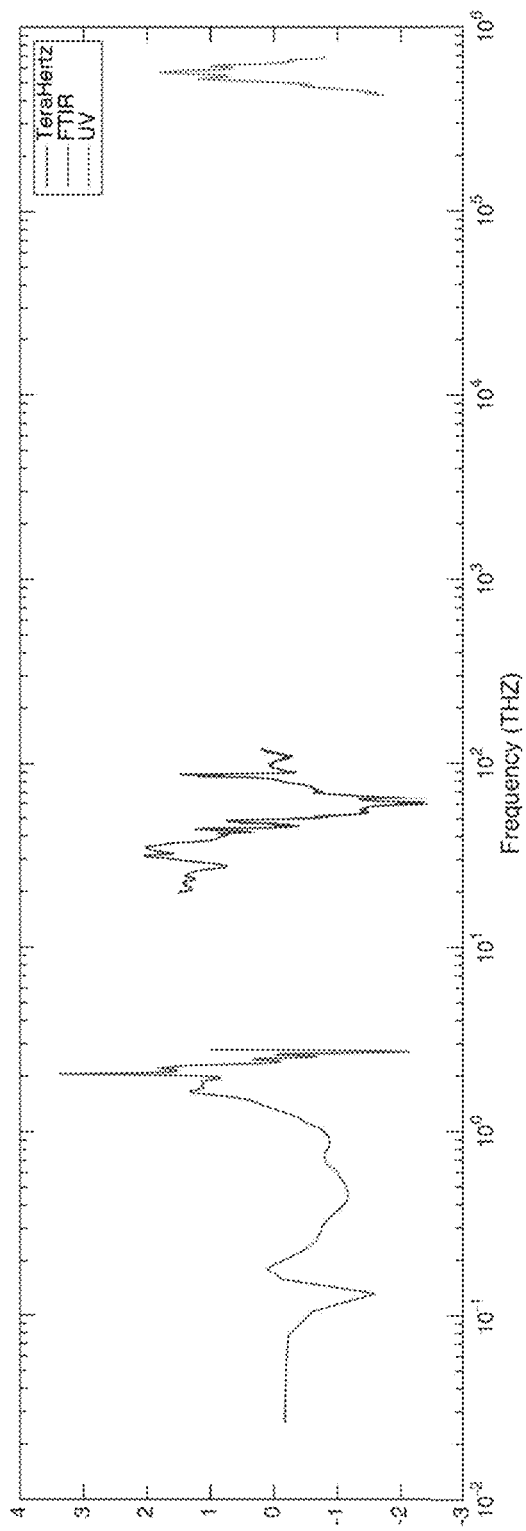
FIG. 15 is a representation of broadband input spectra of one source rock sample spanning terahertz (THz), IR, and ultraviolet (UV) bands.

Multiple measurements, each preprocessed accordingly, can be integrated across the wavenumber of frequency bands, which constitute a high-dimensional nominal input space. An example of such a broadband input spectra is shown in FIG. 15 that shows the full spectra of one source rock sample, spanning THz, IR and UV band (magnitudes in each band as shown are centered and normalized).

Referring to FIG. 13, this processed data is subject to feature extraction step 1302, which includes sparse band selection and dimension reduction. The spectra can be clustered or classified using annotated samples from the database, and then a feature ranking algorithm can be applied to obtain the most informative spectral patterns in a reduced feature space. To elaborate, spectral measurements are mapped into some reduced feature space that captures salient spectral patterns. Then, target attributes such as maturity and organofacies profile are set to sense or predict properties of a source rock sample. A subset of database samples is selected from the curated source rock database as input. Finally, feature selection algorithms are utilized to compute the weights for wavenumber/frequency bands from the selected database samples. Data from step 1302 is then processed through three separate steps. The step 1303 of developing sensing bands for prediction of maturity and organofacies profile includes band selection and optimization through feature ranking. This step is summarized as a mathematical expression representing steps 306, 308, and 310 in FIG. 3, under specific targets for prediction or classification. For the purpose of maturity and organofacies prediction, the value theta θ represents the minimal subset of spectral bands to choose that for the database samples with known maturity or organofacies, they maximize the likelihood of successful prediction. The minimal set is expressed in terms of the constraints that the vector p_norm is less than r. The likelihood of successful prediction is represented by the log p(maturity, organofacies|θ). Selected bands are most informative to the chosen target attributes such as particular level of maturity or organofacies profile, or contribute most to distinguish differences in the target source rock sample. Selected bands will also subject to feasibility constraints of sensor design and deployment. Optimal maturity or organofacies attributes are determined in step 1304. Source rock classification, in step 1305, includes utilization of several classification algorithms such as unsupervised clustering, supervised Latent Dirichlet Allocation (sLDA), or support vector machine modelling. Data and constraints from steps 1303, 1304, and 1305 are utilized in the prediction of the maturity of the source rock sample or the organofacies profile through modelling methodologies such as support vector regression, as in step 1306.

Figure 16A:
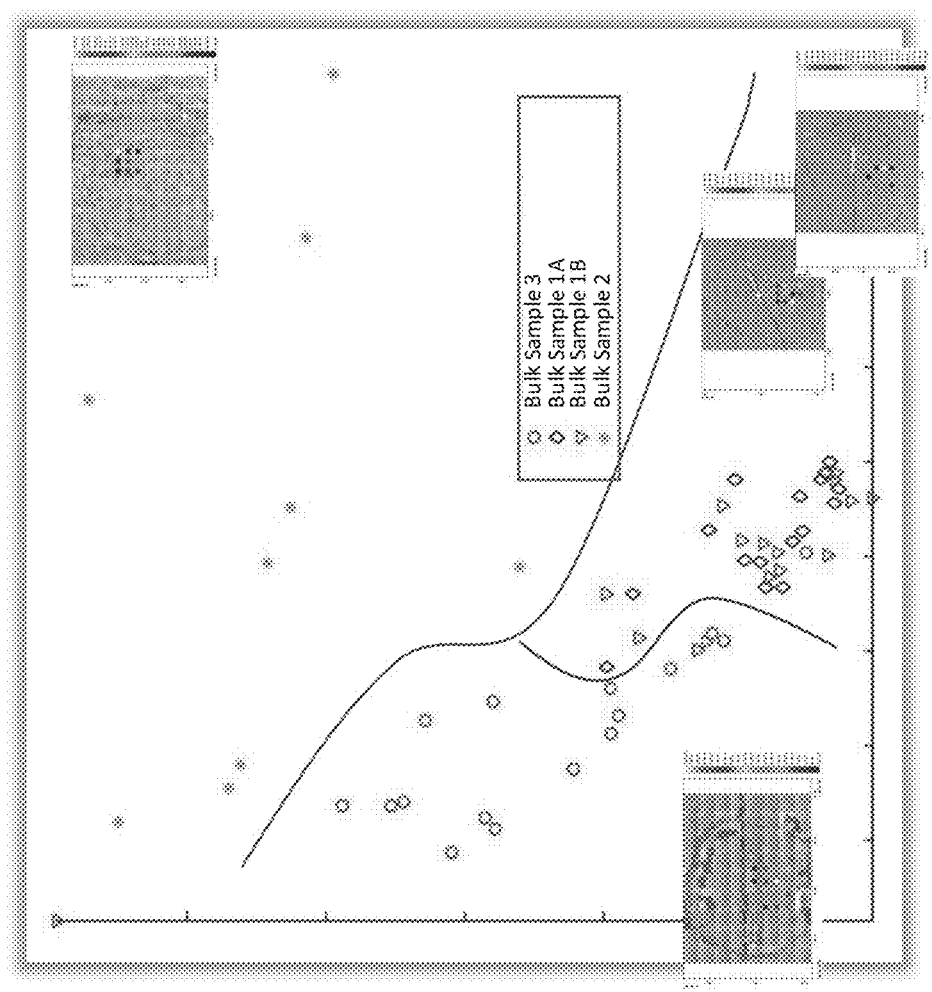
FIGS. 16A and B depict two representations of the clustering of source rock samples in reduced dimensional space.
Figure 16B:
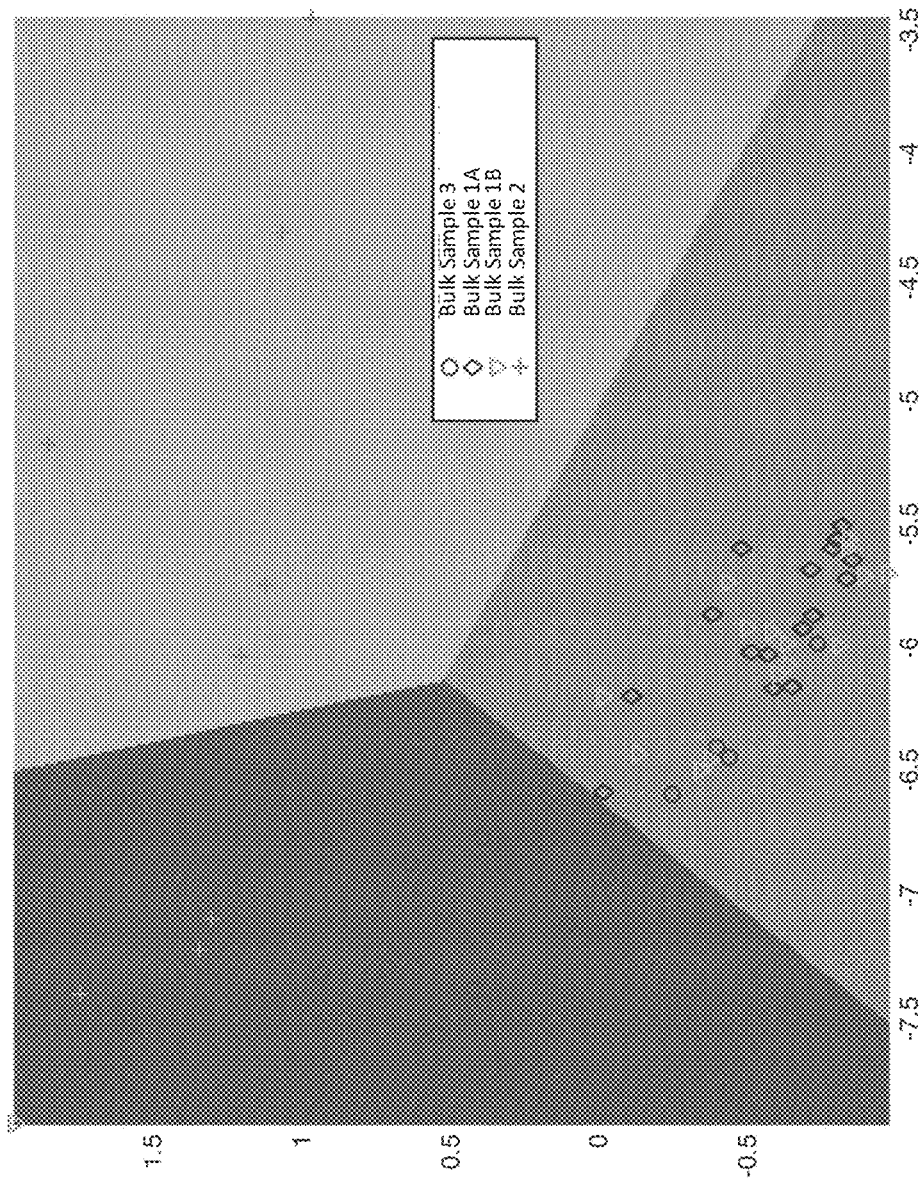

FIGS. 16A and B depict two representations of the clustering of source rock samples in reduced dimensional space. In a clustering based maturity prediction model, spectra are mapped into a reduced feature space that captures salient spectral patterns. Samples are clustered into groups, where source rock samples are similar to each other within each group but different across groups. Maturity specific features and cluster structures are derived to determine both the relevant wavenumber band and the representative spectral patterns. Maturity of a new sample is then predicted from the cluster(s), where the existing spectra are most similar to that of the new sample. This process can be done over accessible subset of bands, or fused over a multitude of measurements. As an example, FIGS. 16A and 16B were obtained via K-means clustering algorithm. Results using hierarchical clustering are provided in FIG. 17 and FIGS. 19 A and B.

Figure 17:
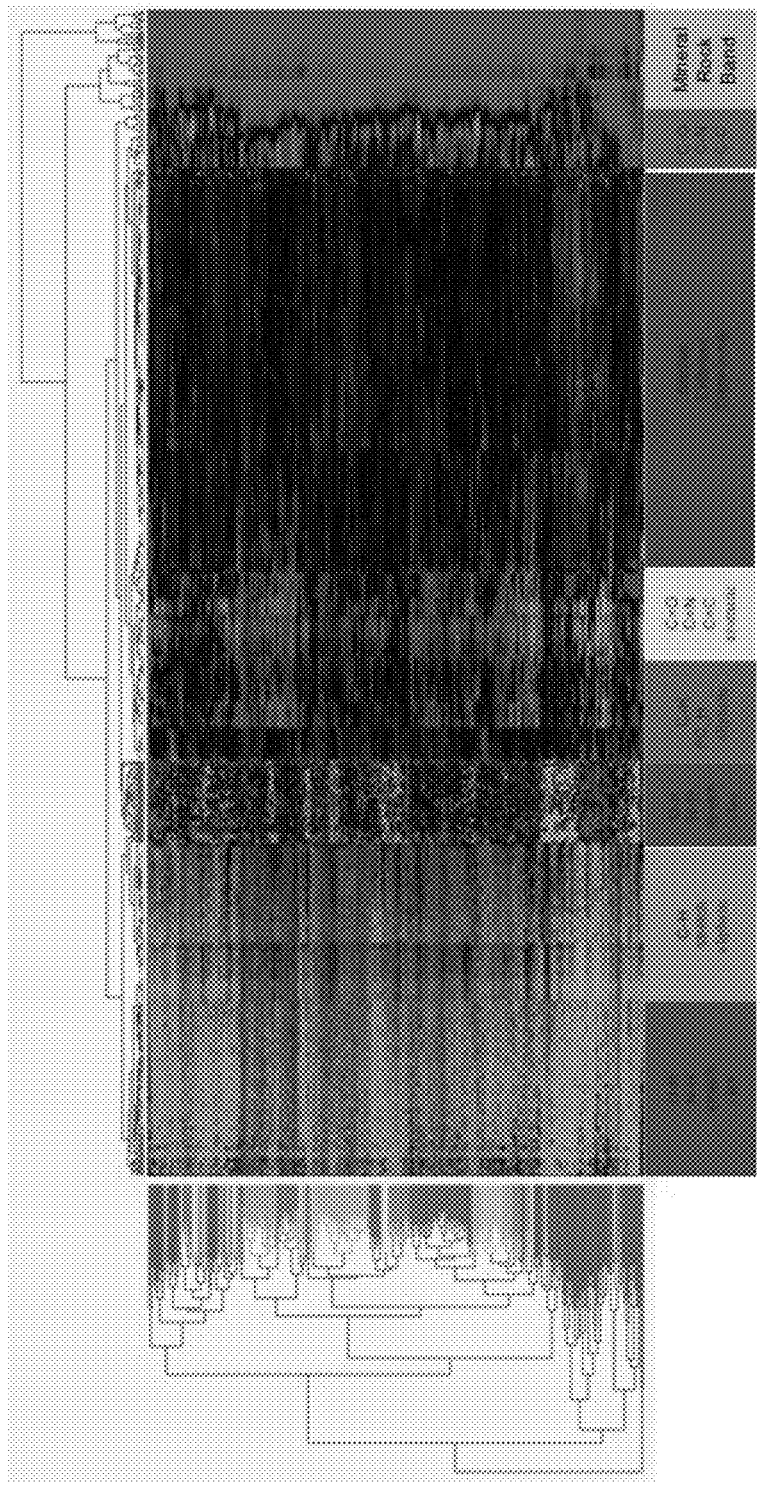
FIG. 17 is a hierarchical biclustering plot.

In a hierarchical bi-clustering based maturity prediction model, samples are clustered according to spectra similarity. Spectra bands are clustered based on their amplitude distribution across the entire sample data sets. Heat map corresponds to the spectra patterns (in the sorted coordinates) that contribute to clustering can be generalized to include various types of measurements, such as fluorescence, THz, and ESR. FIG. 17 is a hierarchical biclustering plot. Each row of the main heat map corresponds to one sample, and each column a particular wavenumber on the spectra. The color scale is mapped from the pre-processed spectra. Taking the preprocessed broadband spectra as input, the algorithm groups and sorts both the samples and the spectral frequencies based on certain distance metric of choice. The tree structure on the top corresponds to the clustering of different spectral frequency or wavenumbers. And the tree structure on the left represents the clustering of different source rock samples. Similar samples are grouped under adjacent leaves of the tree, same with spectral frequencies. For the particular example shown in FIG. 17, the spectral frequencies are grouped by the algorithm in such a way that they form bands that are associated with various mineral and organic contents in the sample source rocks, as well as the molecular structure of the organic matters, as labeled in the color-coded blocks in FIG. 17. By including new samples into the database, these results can provide a clustering of the new sample together with existing samples with known maturity and organofacies, as well as the particular sub-bands that contribute to that clustering structure. This information can be used to determine more granular information such as mineral content and molecular structures associated with particular maturity or organofacies.

These methods of source rock prediction facilitate the geochemical characterization of unconventional reservoirs and provide predictive tools that will allow those in field operations to more accurately assess reservoir quality and recovery potential, and also assess whether production from a given field can be enhanced. Analysis of the samples collected from wells and core samples can also provide critical information in exploration and development for better assessment of reservoir potential.

Example 2

The following example is a method for selection and optimization of the sensing bands. Input is typically from the curated source rock database. Sensing bands are selected and optimized with specific target attributes, such as particular range of source rock maturity or a particular organofacies profile. Bands are selected to provide the most information to the chosen target attributes, or contribute most to distinguish differences in the target source rock sample. Band selection/optimization can be achieved through feature ranking and can also be subject to feasibility constraints of sensor design and deployment.

Figure 18:
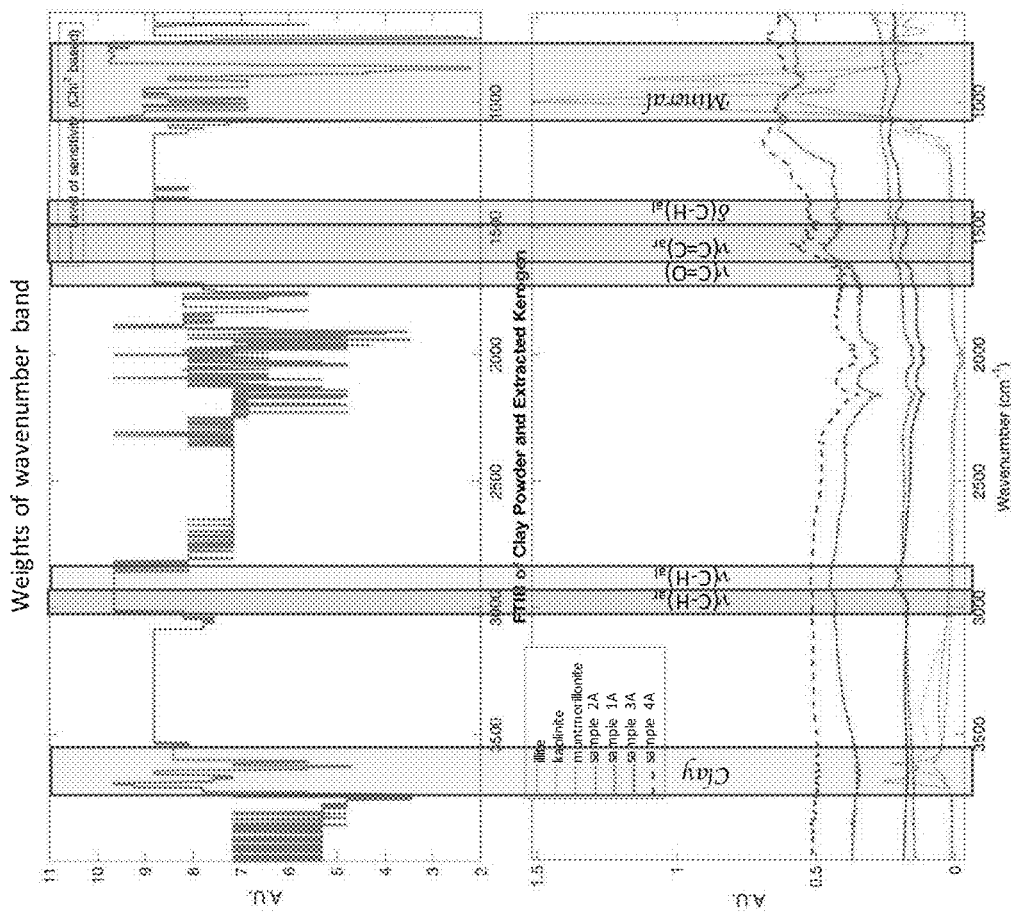
FIG. 18 is a representation of the alignment of the weights of the ranked features from FTIR spectral measurements with the spectroscopic wavenumber bands to differentiate various clays, minerals and kerogen at different maturity levels.

In this example of sensing band optimization, bands were selected to differentiate clay from kerogen at different maturity levels. Feature selection algorithms were applied to compute the weights for each frequency/wavenumber point. FIG. 18 is a representation of the alignment of the weights of the ranked features from FTIR spectral measurements with the spectroscopic wavenumber bands to differentiate various clays, minerals and kerogen at different maturity levels. The top panel of FIG. 18 shows resulting weights for the FTIR wavenumber spectra of the samples. The bottom panel of FIG. 18 shows the FTIR spectra for the various samples. The results consist of a set of weight for each frequency/wavenumber point; the higher the weight on the Y-axis in the top panel of FIG. 18, the more sensitive the selected band is to the target profile. The bands with highest weight coincide with the known bands indicative of hydrocarbon, clay and minerals shown in the lower panel of FIG. 18. Several methods used to achieve a target clustering, classification or prediction goal through feature ranking algorithms, are described in the publication, "Feature Selection: A Data Perspective", by Jundong Li, Kewei Cheng, Suhang Wang, Fred Morstatter, Trevino Robert, Jiliang Tang, and Huan Liu (2016), available at https://arxiv.org/pdf/1601.07996v4.pdf. The optimal sensing bands were chosen from those with highest sensitivity and also feasible for sensor design and deployment. For example, the sensing band for clay was determined to be above 3500 cm$^{-1}$, while the sensing band for minerals was around 450 to 1050 cm$^{-1}$.

Example 3

Figure 19A:
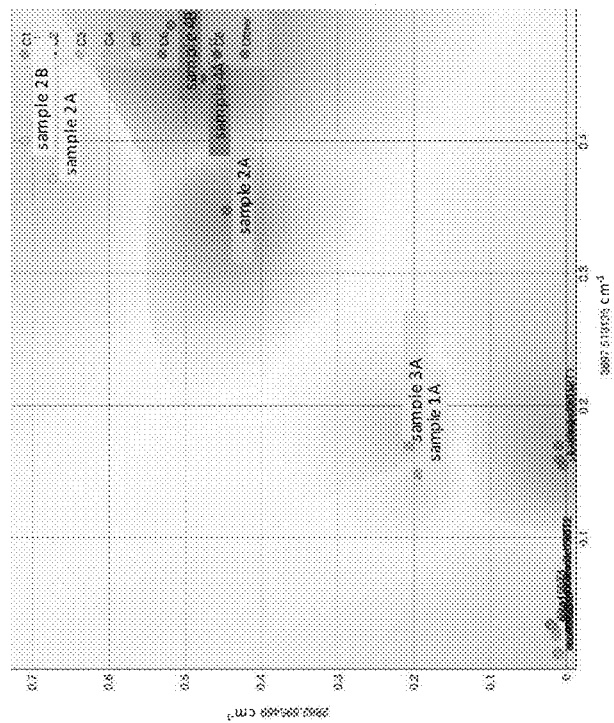
FIGS. 19A and 19B are representations of cluster map of FTIR spectra from different samples projected on selected wavenumber axes.
Figure 19B:
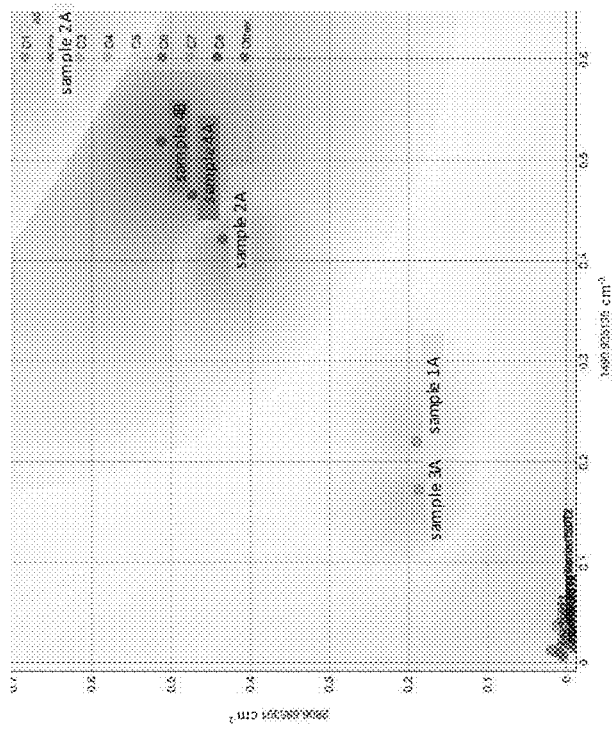
Figure 19C:
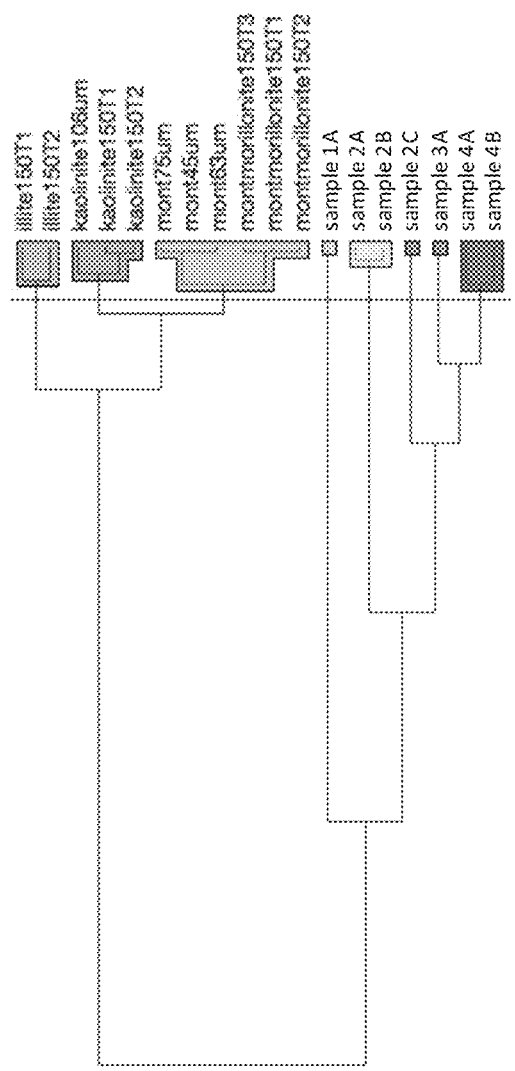
FIG. 19C is an example dendrogram obtained from hierarchical clustering of sample FTIR spectra of 18 different types of samples.

The following example is a method for clustering of source rock samples via hierarchical clustering. Samples are clustered into groups, where source rock samples are similar to each other within each group but different across groups. Maturity specific features and cluster structures are derived to determine both the relevant wavenumber band and the representative spectral patterns. FIGS. 19A and 19B are representations of cluster map of the FTIR spectra from different samples projected on selected wavenumber axes. The clustering was done in a high dimensional space defined by the wavenumber band. FIG. 19A shows the clustering results using spectral wavenumber 1490.9 cm$^{-1}$ (x axis) and 2806.6 cm$^{-1}$ (y axis). FIG. 19B shows the same clustering results in terms of two different spectral wavenumber locations, which are 3697 cm$^{-1}$ for x axis and 2862.5 cm$^{-1}$ for y axis. When projected in these two different coordinate systems, the same clustering results will have different appearance due to the different effects from these wavenumber bands. The samples here include known clay materials—illite (C1), kaolinite (C2), montmorillonite (C3), and extracted kerogen at different maturity levels in ascending order—Sample 3A (C7), Sample 1A (C4), Sample 2A (C5 and C6) and Sample 4A and 4B (C8). FIG. 19C is an example dendrogram obtained from hierarchical clustering of sample FTIR spectra of 18 different types of samples.

Each of these samples were then run as test samples to determine the prediction power of the model. Classification was done using different learning algorithms, such as support vector machine (SVM) regression, Random Forest®, nearest neighbor analysis, and Adaptive Boosting® (also known as AdaBoost®), and their performance was evaluated using four error measures, as presented in Table 3.

TABLE 3

| Method | Mean Square Error (MSE) | Root Mean Square Error (RMSE) | Mean Absolute Error (MAE) | Coefficient of Determination (R2) |
|---|---|---|---|---|
| Nearest Neighbor | 0.139 | 0.373 | 0.200 | 0.791 |
| AdaBoost ® | 0.049 | 0.220 | 0.088 | 0.927 |
| Random Forest ® Regression | 0.064 | 0.252 | 0.128 | 0.904 |
| SVM Regression | 0.708 | 0.841 | 0.738 | −0.067 |

Figures 20A, 20B:
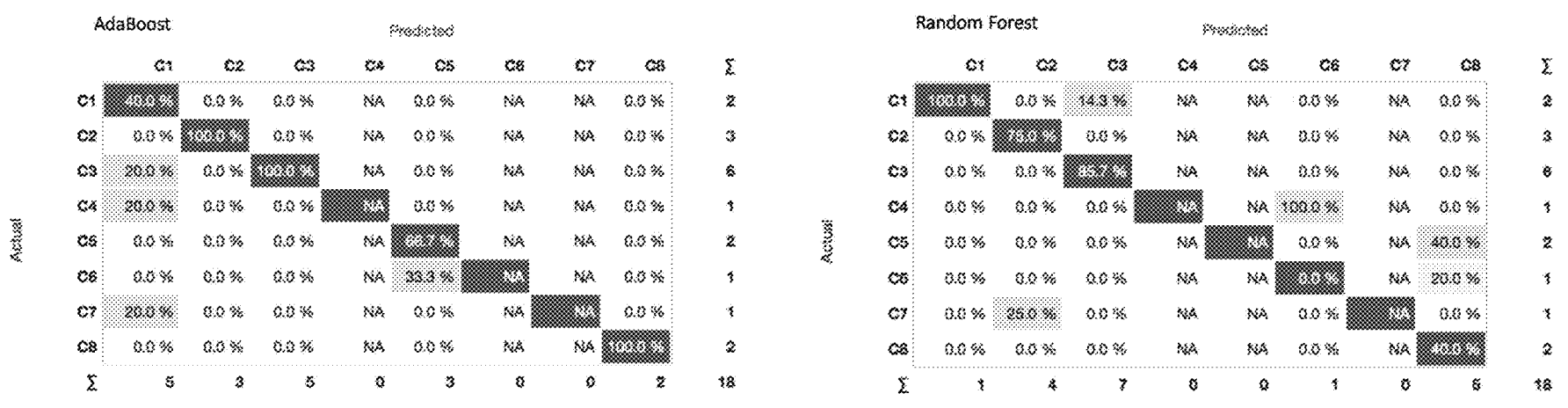

The two highest performing predictors, Adaptive Boosting® and Random Forest® were chosen for maturity prediction and the results are presented in FIGS. 20A and 20B. The predicted results by Adaptive Boosting® (as shown in FIG. 20A) and Random Forest® methods (as shown in FIG. 20B) are plotted against known values for clay materials—illite (C1), kaolinite (C2), montmorillonite (C3), and extracted kerogen at different maturity levels in ascending order—Sample 3A (C7), Sample 1A (C4), Sample 2A (C5 and C6) and Sample 4A (C8).

As previously discussed, maturity level of source rocks and kerogen is represented by several quantities such as Vitrinite Reflectance (Ro %), Hydrogen Index (HI), Pyrolysis Tmax, and atomic H/C ratio. In this example, the ratio of Hydrogen Index (HI) to Vitrinite Reflectance (Ro %) was chosen as the predictor of the maturity. The Adaptive Boosting® and Random Forest® regression models were utilized to predict the HI-Ro % index for the various samples. FIG. 21 presents the maturity index (HI-Ro % ratio) as predicted from FTIR spectra of source rock samples by two different learning algorithms—Adaptive Boosting® and Random Forest® methods as compared to the maturity index obtained by conventional methods of processing the various source rocks. As shown in FIG. 21, these models delivered an extremely high level of predictability of the maturity of the samples.

While these examples have been described using FTIR data, these methods can be applied to other data acquired from THz, ESR, and fluorescence spectroscopy, and other spectral and optical measurements of source rocks.

Example 4

An example of a component of a data acquisition device, a pyroelectric detector, is depicted in FIGS. 22A and 22B. Pyroelectric detectors are not sensitive to high background temperature; and they respond only to temperature change, making them suitable for downhole application. FIG. 22A presents a simplified thermal model and FIG. 22B represents the equivalent electrical circuit, where α is the absorption coefficient, $H_P$ the heat capacity, $G_T$ the thermal conductance, $T_A$ is the ambient temperature. As the amount of light changes due to reflections/transmission into a sample, the amount of heat generated will change to cause a small charge variation into a pyroelectric material such as lithium tantalate. As shown in FIG. 22A, the radiation flux Os is absorbed and causes a change in temperature $\Delta T_P$ in the pyroelectric element. The thermal to electrical conversion is due to pyroelectric effect, whereby the temperature change $\Delta T_P$ alters the charge density $\Delta Q_P$ on the electrodes. As shown in FIG. 22B, the electrical conversion often follows in which the signal is amplified and converted into a voltage. Equation 1 presents the temperature difference for the small circuit shown in FIG. 22B.

$$\Delta T_P = \frac{\alpha \tau_F \Phi_S}{\sqrt{G_T^2 + \omega H_P^2}} \quad \text{[Equation 1]}$$

$\Delta T_P$ will be maximized when $\alpha \tau_F$ is maximized and $G_T$ and $H_P$ are minimized. In practice, a compromise will be required. In some applications, a large signal to noise ratio is required for trace detection, while in other application a high spectral resolution is required, such as for clay identification. Depending on the application, a signal to noise ratio of 10000 to 100 were reported with a tunable filter in collimated geometry for high signal to noise ratio and focused optics for high spectral resolution.

Figure 23:
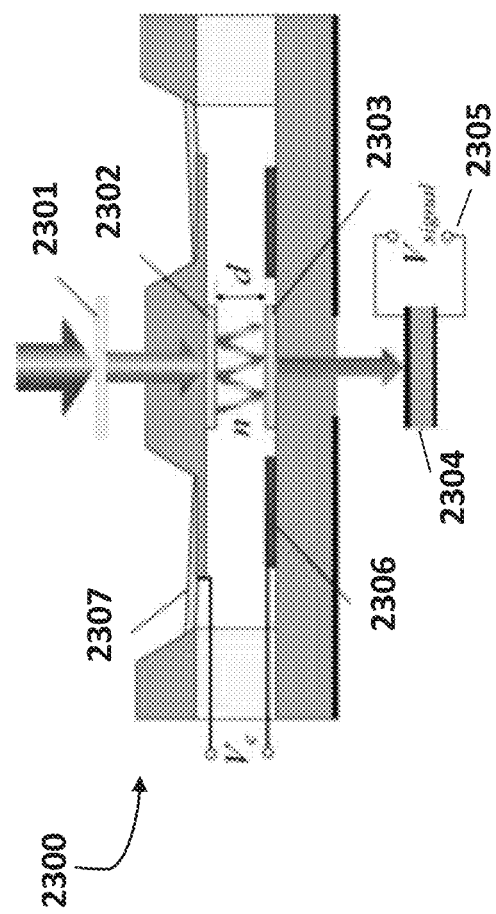
FIG. 23 is a diagrammatic representation of an apparatus containing a commercial pyroelectric detector integrated with a tunable filter, according to an embodiment.

FIG. 23 shows an apparatus 2300 containing a commercial pyroelectric detector integrated with a tunable filter. The filter 2301 can be adjusted to particular wavelengths of interest: 2703 nm for Kaolinite, 3496 nm for Aliphatic group, 2923 nm for Smectite, and so on. In an embodiment, the filter 2301 can be a wide bandpass filter. This apparatus also includes a movable reflector 2302 and a fixed reflector 2303. The apparatus includes pyroelectric detector 2304 consisting of an array of several pyroelectric elements, each with a fixed filter adjusted for a specific wavelength, so that the relatively fragile MEMS mechanics for tuning the filter would not be needed. Such fragile mechanics would make the sensor unsuitable for deployment in a downhole tool, especially if the tool interior was pressure compensated and filled with an insulating liquid. The pyroelectric detector 2304 is coupled to an electric circuit 2305. This apparatus also includes control electrodes 2306 and spring suspensions 2307.

Figure 24:
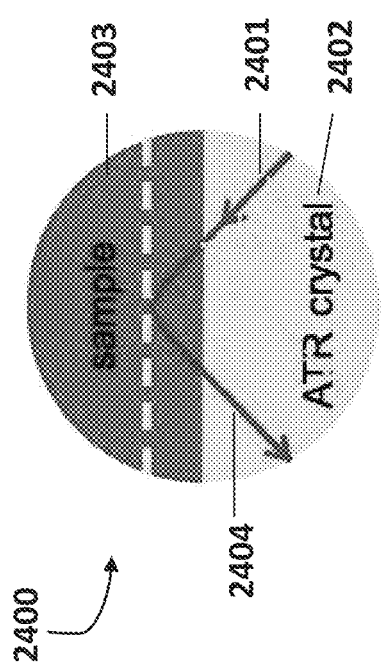
FIG. 24 is a diagrammatic representation of a single bounce configuration of an attenuated total reflectance (ATR) unit, according to an embodiment.
Figure 25:
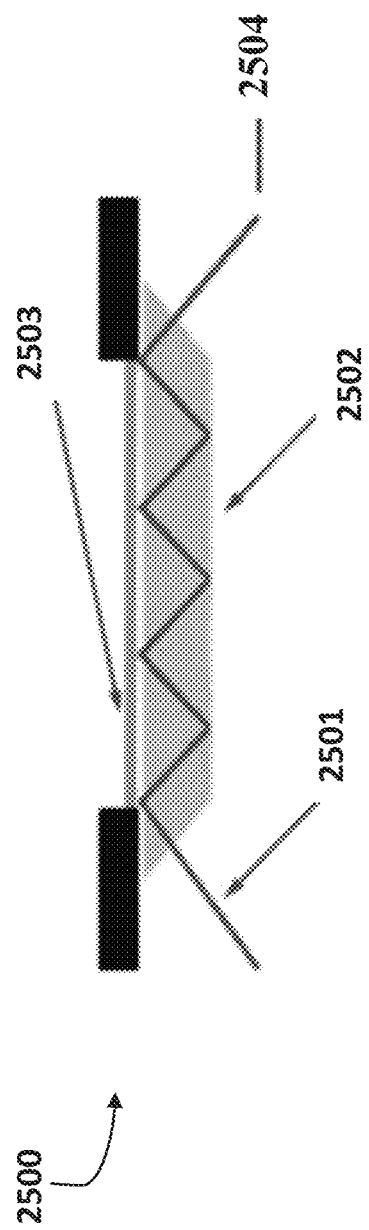
FIG. 25 is a diagrammatic representation of a multi-bounce configuration of an attenuated total reflectance (ATR) unit, according to an embodiment.

FIGS. 24 and 25 depict two configurations of sample measurements. The attenuated total reflectance (ATR) method is chosen in this embodiment. A single bounce ATR unit 2400 is depicted in FIG. 24, where an IR beam 2401 from a spectrometer is internally reflected in the ATR crystal 2402 and interacts with the sample 2403 at the crystal interface. The reflected IR beam 2404 is analyzed to determine the interaction of an evanescent wave with the sample and obtain the absorption spectrum. A waveguide technique with multiple bounces occurs in ATR unit 2500, as depicted in FIG. 25. Incoming light beam 2501 undergoes multiple internal reflections inside an ATR element 2502, which is constructed from special prisms. A broad sample interface provides for greater contact with the sample 2503 and is useful for weak absorbers and dilute samples. The exiting IR beam 2504 is directed to a detector in the IR spectrometer. The detector records the IR beam and generates the infrared spectrum. FIG. 8A and FIG. 8B are examples of infrared spectra of several source rock samples and pure clays. There are distinctive peaks for kaolinite, illite and Na Montmorilonite (Smectite). These clays could be distinguished by looking at each specific clay wave number in the region of 3800 to 3000 $cm^{-1}$. Kaolinite has two distinct peaks at around 3400 $cm^{-1}$ while illite has a sharp peak at 3450 $cm^{-1}$ followed by a broad peak at 3200 $cm^{-1}$.

Example 5

Figure 28A:
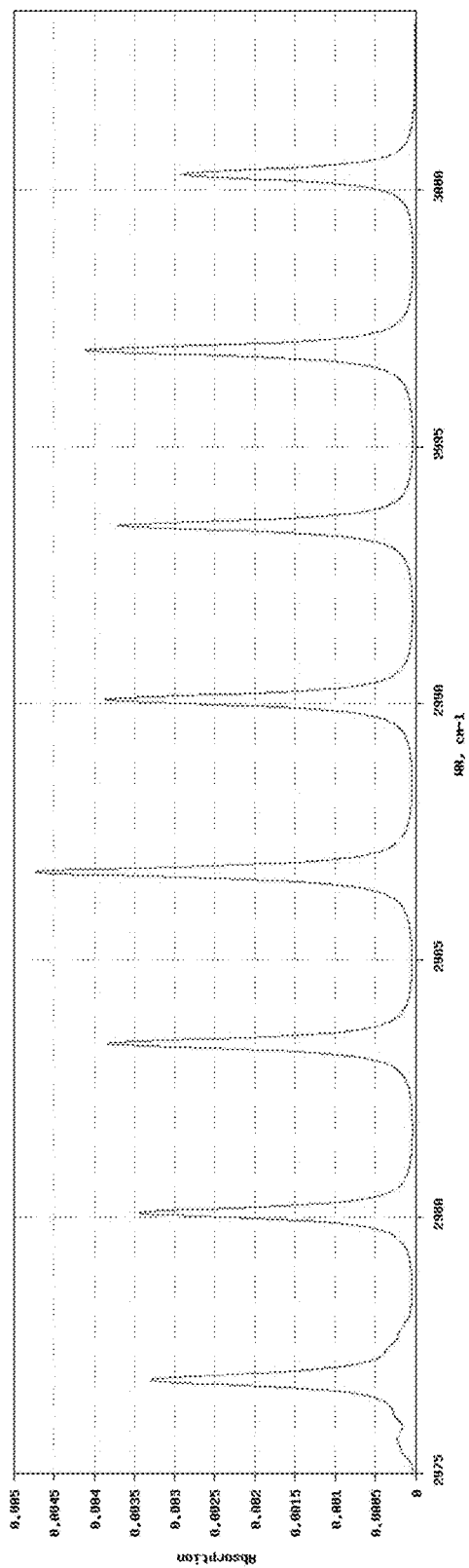
FIGS. 28A and 28B are representations of an IR spectrum obtained using ethane and the associated system calibration spectrum respectively, according to an embodiment.
Figure 28B:
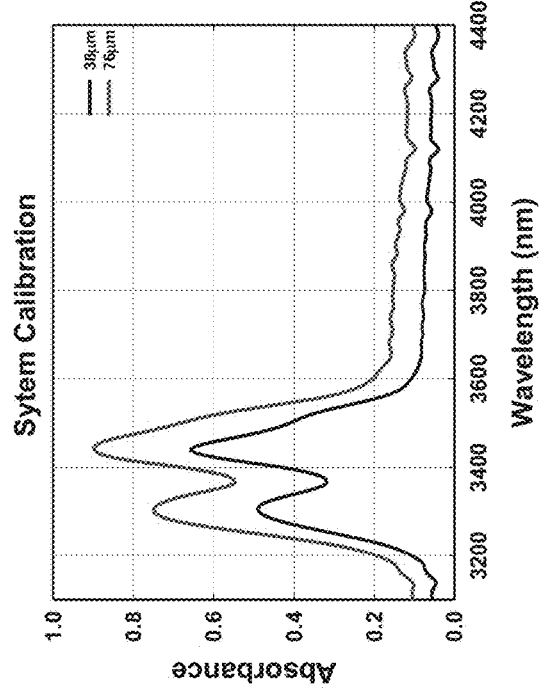

Gas-in-place (GIP) is the volume of gas stored within a specific bulk reservoir rock volume. As cuttings are transported to the surface, some of the gas escapes into the drilling mud. This lost amount of gas leads to errors in GIP estimation. FIG. 26 is a diagrammatic representation of a GIP data acquisition device using a pyroelectric sensor. The apparatus 2600 has a gas inlet 2601 and a gas outlet 2602 for managing the entry and exit of the gas sample through the gas sample chamber 2603. A light source 2604 is placed at one end of the gas sample chamber 2603, and a pyroelectric detector 2605 is placed at the other end of the gas sample chamber 2603. The selected sensor performs well at elevated temperatures, and the footprint of the apparatus has been reduced to fit in a logging while drilling (LWD) tool or production logging tool (PLT). The apparatus is also significantly lower in cost as compared with current GCMS devices, and certain of the GCMS devices are large and not suitable for high temperature use. Gas released from drilling fluids or cuttings can be measured in situ to estimate reserves in place and determine maturity of the source layer. FIGS. 27A, 27B, and 27C are photographs of laboratory prototypes of the GIP data acquisition device 2600, a light source 2604, and a pyroelectric detector 2605, respectively. FIGS. 28A and 28B are an IR spectrum obtained using ethane and the associated system calibration spectrum respectively. Preliminary results indicate this system has a sensitivity of 3 parts per million (3 milligrams/liter) and also provides for the detection of $C_1$-$C_4$ and their ratios.

The devices described in these examples provide IR spectroscopy information about downhole rocks and fluids in situ and at near reservoir conditions. This information includes mineralogy, free water vs bounded water in clays, maturity. It can detect bitumen and pyrobitumen. It can distinguish aromatic vs aliphatic hydrocarbons. It can detect composition of wellbore fluids. In situ measurements are difficult due to poor high temperature performance of the semiconductor materials used in photodetectors. Size requirements preclude in situ measurements using large laboratory size equipment. This disclosure addresses the temperature problem by using a pyroelectric sensor and miniaturizes the spectrometer by using an integrated tunable filter. The package can fit in a wireline tool and it is low cost such that it could be deployed in permanent sensing applications.

Example 6

Figure 29:
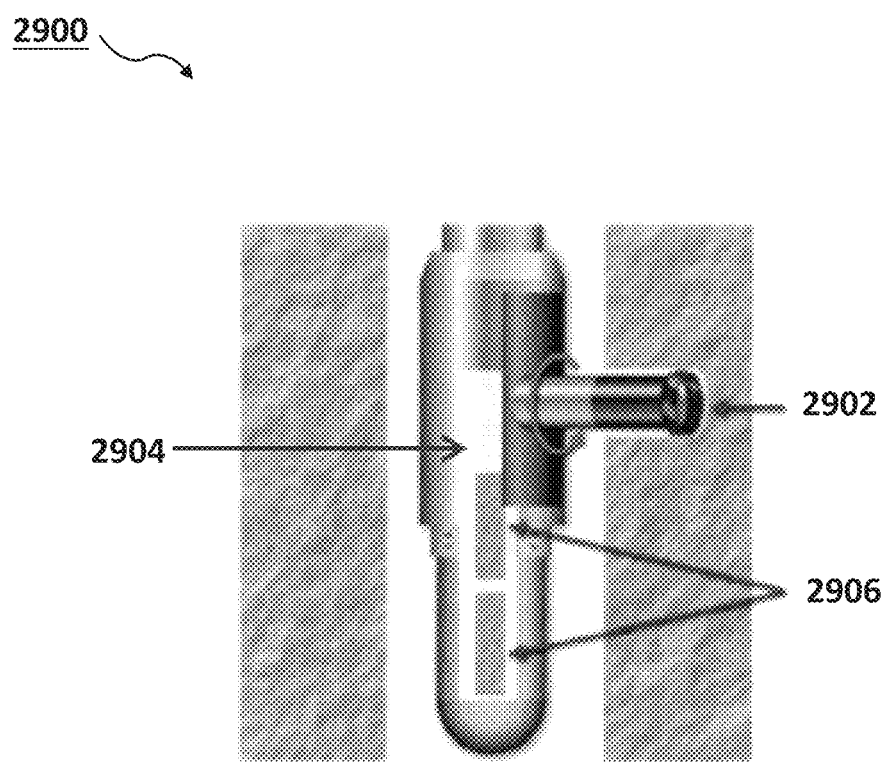
FIG. 29 is a diagrammatic representation of a sampling device, according to an embodiment.

Devices are described here to facilitate sampling for drilling fluids/solids applicable in LWD application as well as in logging. FIG. 29 is a diagrammatic representation of a sampling device 2900. The device 2900 includes a sampling inlet 2902 and a sample acquisition chamber 2904. The sampling inlet 2902 is designed to allow the passage of sample retrieval devices and samples from the environment of the device. The sampling inlet 2902 can be designed to accommodate filters to obtain certain sized samples or fluids. The sample acquisition chamber 2904 can be equipped to store the samples 2906 without loss of integrity until further processing. The sample acquisition chamber 2904 can be equipped to place the sample in contact with in situ data acquisition devices for further processing.

Further modifications and alternative embodiments of various aspects of the apparatuses and methods disclosed here will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims.

The foregoing descriptions of methods, apparatuses, and results obtained using them are provided merely as illustrative examples. Descriptions of the methods are not intended to require or imply that the steps of the various embodiments must be performed in the order presented. As will be appreciated by one of ordinary skill in the art, the steps in the foregoing embodiments may be performed in any order. Words such as "then" are not intended to limit the order of the steps; these words are simply used to guide the reader through the description of the methods. Many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function. Various modifications to these embodiments will be readily apparent to those skilled in the art, and the generic principles defined here may be applied to other embodiments without departing from the spirit or scope of the disclosure.

What is claimed is:

1. A computer implemented method of determining maturity of a sample source rock, the method comprising the steps of:
    establishing, by a data analysis engine, communication links with a source rock database and a plurality of data acquisition devices placed in vicinity of a sample source rock, the source rock database containing a first plurality of data acquired from a plurality of representative source rocks and a plurality of properties of the plurality of representative source rocks;
    acquiring, by the data analysis engine, a second plurality of data of a sample source rock from the plurality of data acquisition devices; and
    analyzing, by the data analysis engine, the second plurality of data using a predictive correlation to determine maturity of the sample source rock, the analyzing comprising determining a spectroscopic wavenumber band for the first plurality of data and at least one of the plurality of properties to differentiate each type of the plurality of representative source rocks, the determining comprising computing a plurality of non-zero weights for a respective plurality of wavenumber points of the spectroscopic wavenumber band, the plurality of non-zero weights based on a sensitivity of the respective plurality of wavenumber points of the spectroscopic wavenumber band to the at least one of the plurality of properties, such that a higher weight of the plurality of non-zero weights corresponds to a greater sensitivity of a respective wavenumber point;
    wherein the predictive correlation is generated, by the data analysis engine, by applying a machine learning model to correlate the first plurality of data acquired from the plurality of representative source rocks with the plurality of properties of the plurality of representative source rocks.

2. The computer implemented method of claim 1, wherein the plurality of data acquisition devices includes a spectrometer comprising a light source, a pyroelectric detector, and a component to reflect light from the sample source rock and direct reflected light to the pyroelectric detector.

3. The computer implemented method of claim 2, wherein the pyroelectric detector is integrated with a tunable filter.

4. The computer implemented method of claim 2, wherein the component to reflect light from the sample source rock and direct reflected light to the pyroelectric detector is an attenuated total reflectance unit.

5. The computer implemented method of claim 1, further comprising the step of
    preparing the second plurality of data before the step of analyzing the second plurality of data by the data analysis engine by implementation of one or more of outlier detection, baseline correction, peak enhancement, and normalization.

6. The computer implemented method of claim 1, further comprising the steps of
    storing, by the data analysis engine, the first plurality of data of a sample source rock and the determined maturity of the sample source rock in a source rock database.

7. The computer implemented method of claim 1, wherein the plurality of properties of the plurality of representative source rocks includes kerogen typing and elemental compositions.

8. The computer implemented method of claim 1, wherein the first plurality of data includes two or more of location data, spectral measurements, and optical measurements acquired from the plurality of representative source rocks.

9. The computer implemented method of claim 8, wherein the spectral measurements include one or more of measurements obtained from Fourier Transform Infrared spectroscopy, Electron Spin Resonance spectroscopy, terahertz spectroscopy, and Ultraviolet spectroscopy.

10. The computer implemented method of claim 8, wherein the first plurality of data further includes pyrolysis data.

11. The computer implemented method of claim 10, wherein the pyrolysis data is obtained by Rock-Eval® pyrolysis analysis of the plurality of representative source rocks.

12. The computer implemented method of claim 1, wherein the second plurality of data includes two or more of location data, spectral measurements, and optical measurements acquired from the sample source rock.

13. The computer implemented method of claim 12, wherein the spectral measurements include one or more of measurements obtained from Fourier Transform Infrared spectroscopy, Electron Spin Resonance spectroscopy, terahertz spectroscopy, and Ultraviolet spectroscopy.

14. The computer implemented method of claim 12, wherein the optical measurements include one or more of measurements obtained by fluorescence microscopy and confocal laser scanning microscopy.

15. The computer implemented method of claim 1, wherein the machine learning model is based on one or more of support vector machine, Random Forest®, logistic regression, and Adaptive Boosting algorithms.

16. The computer implemented method of claim 1, further comprising the step of:
    selecting a spectroscopic wavenumber band for operation of the plurality of data acquisition devices in vicinity of the sample source rock.

17. The computer implemented method of claim 16, wherein the spectroscopic wavenumber band for the sample source rock is selected in response to receiving, by the data analysis engine, one or more selections of desired maturity and desired organofacies profile of the sample source rock from a user interface.

18. A system to determine maturity of a sample source rock, the system comprising:
    a plurality of data acquisition devices placed in vicinity of a sample source rock and communicatively coupled to a computing device;
    the computing device coupled to a source rock database via a communication network and configured to:
        obtain a first plurality of data of a sample source rock from the plurality of data acquisition devices; and
        analyze the first plurality of data using a predictive correlation to determine maturity of the sample source rock,
            wherein the predictive correlation is generated by applying a machine learning model to correlate a second plurality of data acquired from a plurality of representative source rocks with a plurality of properties of the plurality of representative source rocks; and
    the source rock database containing the second plurality of data associated with the plurality of representative source rocks, the plurality of properties of the plurality of representative source rocks, and the predictive correlation, wherein the operation of analyze the first plurality of data comprises determining a spectroscopic wavenumber band for the second plurality of data and at least one of the plurality of properties that differentiates each type of the plurality of representative source rocks the determining comprising computing a plurality of non-zero weights for a respective plurality of wavenumber points of the spectroscopic wavenumber band, the plurality of non-zero weights based on a sensitivity of the respective plurality of wavenumber points of the spectroscopic wavenumber band to the at least one of the plurality of properties, such that a higher weight of the plurality of non-zero weights corresponds to a greater sensitivity of a respective wavenumber point.

19. The system of claim 18, wherein the plurality of data acquisition devices is positioned to acquire data of the sample source rock using the spectroscopic wavenumber band.

20. The system of claim 18, further comprising a sample source rock retrieving apparatus to obtain a portion of the sample source rock.

21. The system of claim 18, wherein the plurality of data acquisition devices is positioned to acquire two or more of location data, spectral measurements, and optical measurements.

22. The system of claim 21, wherein the spectral measurements include one or more of measurements obtained from Fourier Transform Infrared spectroscopy, Electron Spin Resonance spectroscopy, terahertz spectroscopy, and Ultraviolet spectroscopy.

23. The system of claim 21, wherein the optical measurements include one or more of measurements obtained by fluorescence microscopy and confocal laser scanning microscopy.

24. The system of claim 18, wherein the plurality of data acquisition devices includes a spectrometer comprising a light source, a pyroelectric detector, and a component to reflect light from the sample source rock and direct reflected light to the pyroelectric detector.

25. The system of claim 24, wherein the pyroelectric detector is integrated with a tunable filter.

26. The system of claim 24, wherein the component to reflect light from the sample source rock and direct reflected light to the pyroelectric detector is an attenuated total reflectance unit.

27. A system to determine maturity of a sample source rock, the system comprising:
    a gas-in-place data acquisition device placed in vicinity of a sample source rock and communicatively coupled to a computing device;
    the computing device coupled to a source rock database via a communication network and configured to:
        obtain a first plurality of data of a sample source rock from the gas-in-place data acquisition device; and
        analyze the first plurality of data using a predictive correlation to determine maturity of the sample source rock,
            wherein the predictive correlation is generated by applying a machine learning model to correlate a second plurality of data acquired from a plurality of representative source rocks with a plurality of properties of the plurality of representative source rocks; and
    the source rock database containing the second plurality of data associated with the plurality of representative source rocks, the plurality of properties of the plurality of representative source rocks, and the predictive correlation, wherein the operation of analyze the first plurality of data comprises determining a spectroscopic wavenumber band for the second plurality of data and at least one of the plurality of properties that differentiates each type of the plurality of representative source rocks the determining comprising computing a plurality of non-zero weights for a respective plurality of wavenumber points of the spectroscopic wavenumber band, the plurality of non-zero weights based on a sensitivity of the respective plurality of wavenumber points of the spectroscopic wavenumber band to the at least one of the plurality of properties, such that a higher weight of the plurality of non-zero weights corresponds to a greater sensitivity of a respective wavenumber point.

28. The system of claim 27, wherein the gas-in-place data acquisition device includes a spectrometer comprising a light source, a pyroelectric detector, a gas inlet, a gas outlet, and a sample chamber.

29. The system of claim 27, wherein the gas-in-place data acquisition device is deployed as part of a logging while drilling assembly.

30. The system of claim 27, wherein the gas-in-place data acquisition device is deployed as part of a wireline logging assembly.

* * * * *